US010111697B2

(12) United States Patent
Mazzuca et al.

(10) Patent No.: US 10,111,697 B2
(45) Date of Patent: Oct. 30, 2018

(54) DEVICE FOR DELIVERING VISCOUS MATERIAL

(71) Applicant: DePuy Synthes Products, Inc., Raynham, MA (US)

(72) Inventors: Michael Mazzuca, North Easton, MA (US); John Voellmicke, Cumberland, RI (US); Michael Gorhan, Mansfield, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 1197 days.

(21) Appl. No.: 14/057,335

(22) Filed: Oct. 18, 2013

(65) Prior Publication Data

US 2014/0046335 A1 Feb. 13, 2014

Related U.S. Application Data

(63) Continuation of application No. 10/947,496, filed on Sep. 22, 2004, now Pat. No. 8,579,908.

(60) Provisional application No. 60/507,290, filed on Sep. 26, 2003.

(51) Int. Cl.
*A61B 17/88* (2006.01)

(52) U.S. Cl.
CPC ...... *A61B 17/8822* (2013.01); *A61B 17/8827* (2013.01); *A61B 17/8825* (2013.01)

(58) Field of Classification Search
CPC ........... A61B 17/8802; A61B 17/8833; A61M 1/0019; B65B 69/0016
USPC ............................................ 606/94; 604/257
See application file for complete search history.

(56) References Cited

U.S. PATENT DOCUMENTS

| | | |
|---|---|---|
| 229,932 A | 7/1880 | Witsil |
| 370,335 A | 9/1887 | Hunter |
| 408,668 A | 8/1889 | Peck |
| 817,973 A | 4/1906 | Hausmann |
| 833,044 A | 10/1906 | Goodhugh |
| 843,587 A | 2/1907 | De Pew |
| 1,175,530 A | 3/1916 | Kirchhoff |
| 1,612,281 A | 12/1926 | Goetz |
| 1,612,996 A | 4/1927 | Waagbo |
| 1,733,516 A | 10/1929 | Rodin |
| 1,894,274 A | 1/1933 | Jacques |
| 1,929,247 A | 10/1933 | Hein |
| 2,067,458 A | 1/1937 | Nichols |
| 2,123,712 A | 7/1938 | Clark |
| 2,283,915 A | 5/1942 | Cole |
| 2,394,488 A | 2/1946 | Rotter |

(Continued)

FOREIGN PATENT DOCUMENTS

| | | |
|---|---|---|
| CN | 1138001 | 12/1996 |
| CN | 1310026 | 8/2001 |

(Continued)

OTHER PUBLICATIONS

Dewijn, J.R., Characterization of Bone Cements, The Institute of Dental Materials Science and Technology and the Dept of Ortho., Catholic University, Netherlands 46:38-51 (1975).

(Continued)

*Primary Examiner* — Anu Ramana

(57) ABSTRACT

Methods and devices are described for delivering a viscous material to a surgical site in a patient while keeping the clinician outside the fluoroscopy field.

20 Claims, 4 Drawing Sheets

(56) References Cited

U.S. PATENT DOCUMENTS

| | | |
|---|---|---|
| 2,425,867 A | 8/1947 | Davis |
| 2,435,647 A | 2/1948 | Engseth |
| 2,497,762 A | 2/1950 | Davis |
| 2,521,569 A | 9/1950 | Davis |
| 2,567,960 A | 9/1951 | Myers |
| 2,745,575 A | 5/1956 | Spencer |
| 2,773,500 A | 12/1956 | Young |
| 2,808,239 A | 10/1957 | Reiffen |
| 2,874,877 A | 2/1959 | Spencer |
| 2,918,841 A | 12/1959 | Poupitch |
| 2,928,574 A | 3/1960 | Wagner |
| 2,970,773 A | 2/1961 | Keryluk |
| 3,058,413 A | 10/1962 | Cavalier |
| 3,063,449 A | 11/1962 | Schultz |
| 3,075,746 A | 1/1963 | Yablonski |
| 3,108,593 A | 10/1963 | Glassman |
| 3,151,847 A | 10/1964 | Broomall |
| 3,198,194 A | 8/1965 | Wilburn |
| 3,216,616 A | 11/1965 | Blankenship, Jr. |
| 3,224,744 A | 12/1965 | Broomall |
| 3,225,760 A | 12/1965 | Di Cosola |
| 3,254,494 A | 6/1966 | Chartouni |
| 3,362,793 A | 1/1968 | Massoubre |
| 3,381,566 A | 5/1968 | Passer |
| 3,426,364 A | 2/1969 | Lumb |
| 3,515,873 A | 6/1970 | Higgins |
| 3,559,956 A | 2/1971 | Gray |
| 3,568,885 A | 3/1971 | Spencer |
| 3,572,556 A | 3/1971 | Pogacar |
| 3,605,745 A | 9/1971 | Hodosh |
| 3,615,240 A | 10/1971 | Sanz |
| 3,674,011 A | 7/1972 | Michel |
| 3,701,350 A | 10/1972 | Guenther |
| 3,750,667 A | 8/1973 | Pshenichny |
| 3,789,727 A | 2/1974 | Moran |
| 3,796,303 A | 3/1974 | Allet-Coche |
| 3,798,982 A | 3/1974 | Lundquist |
| 3,846,846 A | 11/1974 | Fischer |
| 3,850,158 A | 11/1974 | Elias |
| 3,867,728 A | 2/1975 | Stubstad |
| 3,873,008 A | 3/1975 | Jahn |
| 3,875,595 A | 4/1975 | Froning |
| 3,896,504 A | 7/1975 | Fischer |
| 3,901,408 A | 8/1975 | Boden |
| 3,921,858 A | 11/1975 | Bemm |
| 3,931,914 A | 1/1976 | Hosaka |
| 3,942,407 A | 3/1976 | Mortensen |
| 3,976,060 A | 8/1976 | Hildebrandt |
| 3,993,250 A | 11/1976 | Shure |
| 4,011,602 A | 3/1977 | Rybicki |
| 4,062,274 A | 12/1977 | Knab |
| 4,077,494 A | 3/1978 | Spaude |
| 4,079,917 A | 3/1978 | Popeil |
| 4,090,640 A | 5/1978 | Smith |
| 4,093,576 A | 6/1978 | deWijn |
| 4,105,145 A | 8/1978 | Capra |
| 4,115,346 A | 9/1978 | Gross |
| 4,146,334 A | 3/1979 | Farrell |
| 4,168,787 A | 9/1979 | Stamper |
| 4,170,990 A | 10/1979 | Baumgart |
| 4,180,070 A | 12/1979 | Genese |
| 4,185,072 A | 1/1980 | Puderbaugh |
| 4,189,065 A | 2/1980 | Herold |
| 4,198,383 A | 4/1980 | Konsetov |
| 4,198,975 A | 4/1980 | Haller |
| 4,204,531 A | 5/1980 | Aginsky |
| 4,239,113 A | 12/1980 | Gross |
| 4,250,887 A | 2/1981 | Dardik |
| 4,257,540 A | 3/1981 | Wegmann |
| 4,268,639 A | 5/1981 | Seidel |
| 4,274,163 A | 6/1981 | Malcom |
| 4,276,878 A | 7/1981 | Storz |
| 4,277,184 A | 7/1981 | Solomon |
| 4,298,144 A | 11/1981 | Pressl |
| 4,309,777 A | 1/1982 | Patil |
| 4,312,343 A | 1/1982 | LeVeen |
| 4,313,434 A | 2/1982 | Segal |
| 4,326,567 A | 4/1982 | Mistarz |
| 4,332,254 A | 6/1982 | Lundquist |
| 4,338,925 A | 7/1982 | Miller |
| 4,341,691 A | 7/1982 | Anuta |
| 4,346,708 A | 8/1982 | LeVeen |
| 4,349,921 A | 9/1982 | Kuntz |
| 4,359,049 A | 11/1982 | Redl |
| 4,373,217 A | 2/1983 | Draenert |
| 4,380,398 A | 4/1983 | Burgess |
| 4,400,170 A | 8/1983 | McNaughton |
| 4,403,989 A | 9/1983 | Christensen |
| 4,404,327 A | 9/1983 | Crugnola |
| 4,405,249 A | 9/1983 | Scales |
| 4,409,966 A | 10/1983 | Lambrecht |
| 4,453,539 A | 6/1984 | Raftopoulos |
| 4,474,572 A | 10/1984 | McNaughton |
| 4,475,856 A | 10/1984 | Toomingas |
| 4,476,866 A | 10/1984 | Chin |
| 4,487,602 A | 12/1984 | Christensen |
| 4,494,535 A | 1/1985 | Haig |
| 4,500,658 A | 2/1985 | Fox |
| 4,503,169 A | 3/1985 | Randklev |
| 4,503,673 A | 3/1985 | Schachle |
| 4,522,200 A | 6/1985 | Stednitz |
| D279,499 S | 7/1985 | Case |
| 4,543,966 A | 10/1985 | Islam |
| 4,546,767 A | 10/1985 | Smith |
| 4,554,914 A | 11/1985 | Kapp |
| 4,558,693 A | 12/1985 | Lash |
| 4,562,598 A | 1/1986 | Kranz |
| 4,576,152 A | 3/1986 | Muller |
| 4,588,583 A | 5/1986 | Pietsch |
| 4,593,685 A | 6/1986 | McKay |
| 4,595,006 A | 6/1986 | Burke |
| 4,600,118 A | 7/1986 | Martin |
| 4,605,011 A | 8/1986 | Naslund |
| 4,632,101 A | 12/1986 | Freedland |
| 4,636,217 A | 1/1987 | Ogilvie |
| 4,642,099 A | 2/1987 | Phillips |
| 4,650,469 A | 3/1987 | Berg |
| 4,651,904 A | 3/1987 | Schuckmann |
| 4,653,487 A | 3/1987 | Maale |
| 4,653,489 A | 3/1987 | Tronzo |
| 4,664,298 A | 5/1987 | Shew |
| 4,664,655 A | 5/1987 | Orentreich |
| 4,668,220 A | 5/1987 | Hawrylenko |
| 4,668,295 A | 5/1987 | Bajpai |
| 4,670,008 A | 6/1987 | Von Albertini |
| 4,671,263 A | 6/1987 | Draenert |
| 4,676,655 A | 6/1987 | Handler |
| 4,676,781 A | 6/1987 | Phillips |
| 4,677,140 A | 6/1987 | Shiotsu |
| 4,684,673 A | 8/1987 | Adachi |
| 4,686,973 A | 8/1987 | Frisch |
| 4,697,584 A | 10/1987 | Haynes |
| 4,697,929 A | 10/1987 | Muller |
| 4,704,035 A | 11/1987 | Kowalczyk |
| 4,710,179 A | 12/1987 | Haber |
| 4,714,721 A | 12/1987 | Franek |
| 4,717,383 A | 1/1988 | Phillips |
| 4,718,910 A | 1/1988 | Draenert |
| 4,722,948 A | 2/1988 | Sanderson |
| 4,728,006 A | 3/1988 | Drobish |
| 4,735,616 A | 4/1988 | Eibl |
| 4,737,151 A | 4/1988 | Clement |
| 4,747,832 A | 5/1988 | Buffet |
| 4,758,096 A | 7/1988 | Gunnarsson |
| 4,758,234 A | 7/1988 | Orentreich |
| 4,759,769 A | 7/1988 | Hedman |
| 4,762,515 A | 8/1988 | Grimm |
| 4,767,033 A | 8/1988 | Gemperle |
| 4,772,287 A | 9/1988 | Ray |
| 4,782,118 A | 11/1988 | Fontanille |
| 4,786,184 A | 11/1988 | Berezkina |
| 4,791,150 A | 12/1988 | Braden |
| 4,792,577 A | 12/1988 | Chen |
| 4,804,023 A | 2/1989 | Frearson |

(56) References Cited

U.S. PATENT DOCUMENTS

| | | |
|---|---|---|
| 4,813,870 A | 3/1989 | Pitzen |
| 4,815,454 A | 3/1989 | Dozier, Jr. |
| 4,815,632 A | 3/1989 | Ball |
| 4,820,271 A | 4/1989 | Deutsch |
| 4,826,053 A | 5/1989 | Keller |
| 4,830,227 A | 5/1989 | Ball |
| 4,837,279 A | 6/1989 | Arroyo |
| 4,849,223 A | 7/1989 | Pratt |
| 4,854,312 A | 8/1989 | Raftopoulos |
| 4,854,482 A | 8/1989 | Bergner |
| 4,854,716 A | 8/1989 | Ziemann |
| 4,863,072 A | 9/1989 | Perler |
| 4,869,906 A | 9/1989 | Dingeldein |
| 4,872,936 A | 10/1989 | Engelbrecht |
| 4,892,231 A | 1/1990 | Ball |
| 4,892,550 A | 1/1990 | Huebsch |
| 4,900,546 A | 2/1990 | Posey-Dowty |
| 4,902,649 A | 2/1990 | Kimura |
| 4,904,260 A | 2/1990 | Ray |
| 4,908,017 A | 3/1990 | Howson |
| 4,910,259 A | 3/1990 | Kindt-Larsen |
| 4,927,866 A | 5/1990 | Purrmann |
| 4,932,969 A | 6/1990 | Frey |
| 4,935,029 A | 6/1990 | Matsutani |
| 4,944,065 A | 7/1990 | Svanberg |
| 4,944,726 A | 7/1990 | Hilal |
| 4,946,077 A | 8/1990 | Olsen |
| 4,946,285 A | 8/1990 | Vennemeyer |
| 4,946,901 A | 8/1990 | Lechner |
| 4,961,647 A | 10/1990 | Coutts |
| 4,966,601 A | 10/1990 | Draenert |
| 4,968,303 A | 11/1990 | Clarke |
| 4,969,888 A | 11/1990 | Scholten |
| 4,973,168 A | 11/1990 | Chan |
| 4,973,301 A | 11/1990 | Nissenkorn |
| 4,973,334 A | 11/1990 | Ziemann |
| 4,978,336 A | 12/1990 | Capozzi |
| 4,983,164 A | 1/1991 | Hook |
| 4,994,065 A | 2/1991 | Gibbs |
| 4,995,868 A | 2/1991 | Brazier |
| 5,004,501 A | 4/1991 | Faccioli |
| 5,006,112 A | 4/1991 | Metzner |
| 5,012,066 A | 4/1991 | Matsutani |
| 5,012,413 A | 4/1991 | Sroka |
| 5,015,233 A | 5/1991 | McGough |
| 5,018,919 A | 5/1991 | Stephan |
| 5,022,563 A | 6/1991 | Marchitto |
| 5,024,232 A | 6/1991 | Smid |
| 5,028,141 A | 7/1991 | Stiegelmann |
| 5,035,706 A | 7/1991 | Giantureo |
| 5,037,473 A | 8/1991 | Antonucci |
| 5,049,157 A | 9/1991 | Mittelmeier |
| 5,051,482 A | 9/1991 | Tepic |
| 5,059,193 A | 10/1991 | Kuslich |
| 5,059,199 A | 10/1991 | Okada |
| 5,061,128 A | 10/1991 | Jahr |
| 5,062,128 A | 10/1991 | Katsuragi |
| 5,071,040 A | 12/1991 | Laptewicz, Jr. |
| 5,074,871 A | 12/1991 | Groshong |
| 5,078,919 A | 1/1992 | Ashley |
| 5,092,888 A | 3/1992 | Iwamoto |
| 5,102,413 A | 4/1992 | Poddar |
| 5,106,614 A | 4/1992 | Posey-Dowty |
| 5,108,403 A | 4/1992 | Stern |
| 5,108,404 A | 4/1992 | Scholten |
| 5,112,333 A | 5/1992 | Fixel |
| 5,114,240 A | 5/1992 | Kindt-Larsen |
| 5,116,335 A | 5/1992 | Hannon |
| 5,122,400 A | 6/1992 | Stewart |
| 5,123,926 A | 6/1992 | Pisharodi |
| 5,125,971 A | 6/1992 | Nonami |
| 5,131,382 A | 7/1992 | Meyer |
| 5,141,496 A | 8/1992 | Dalto |
| 5,145,250 A | 9/1992 | Planck |
| 5,147,903 A | 9/1992 | Podszun |
| 5,171,248 A | 12/1992 | Ellis |
| 5,171,278 A | 12/1992 | Pisharodi |
| 5,181,918 A | 1/1993 | Brandhorst |
| 5,188,259 A | 2/1993 | Petit |
| 5,188,604 A * | 2/1993 | Orth ............... A61M 1/10 128/DIG. 13 |
| 5,190,191 A | 3/1993 | Reyman |
| 5,192,327 A | 3/1993 | Brantigan |
| 5,193,907 A | 3/1993 | Faccioli |
| 5,203,773 A | 4/1993 | Green |
| 5,209,753 A | 5/1993 | Biedermann |
| 5,217,147 A | 6/1993 | Kaufman |
| 5,219,897 A | 6/1993 | Murray |
| 5,236,445 A | 8/1993 | Hayhurst |
| 5,242,983 A | 9/1993 | Kennedy |
| 5,252,301 A | 10/1993 | Nilson |
| 5,254,092 A | 10/1993 | Polyak |
| 5,258,420 A | 11/1993 | Posey-Dowty |
| 5,264,215 A | 11/1993 | Nakabayashi |
| 5,268,001 A | 12/1993 | Nicholson |
| 5,269,762 A | 12/1993 | Armbruster |
| 5,275,214 A | 1/1994 | Rehberger |
| 5,276,070 A | 1/1994 | Arroyo |
| 5,277,339 A | 1/1994 | Shew |
| 5,279,555 A | 1/1994 | Lifshey |
| 5,290,260 A | 3/1994 | Stines |
| 5,295,980 A | 3/1994 | Ersek |
| 5,296,305 A | 3/1994 | Baude |
| 5,302,020 A | 4/1994 | Kruse |
| 5,303,718 A | 4/1994 | Krajicek |
| 5,304,147 A | 4/1994 | Johnson |
| 5,304,577 A | 4/1994 | Nagata |
| 5,318,532 A | 6/1994 | Frassica |
| 5,328,262 A | 7/1994 | Lidgren |
| 5,328,362 A | 7/1994 | Watson |
| 5,331,972 A | 7/1994 | Wadhwani |
| 5,333,951 A | 8/1994 | Wakoh |
| 5,334,184 A | 8/1994 | Bimman |
| 5,334,626 A | 8/1994 | Lin |
| 5,336,699 A | 8/1994 | Cooke |
| 5,336,700 A | 8/1994 | Murray |
| 5,344,232 A | 9/1994 | Nelson |
| 5,348,391 A | 9/1994 | Murray |
| 5,348,548 A | 9/1994 | Meyer |
| 5,350,372 A | 9/1994 | Ikeda |
| 5,354,287 A | 10/1994 | Wacks |
| 5,356,382 A | 10/1994 | Picha |
| 5,368,046 A | 11/1994 | Scarfone |
| 5,368,386 A | 11/1994 | Murray |
| 5,370,221 A | 12/1994 | Magnusson |
| 5,372,583 A | 12/1994 | Roberts |
| 5,374,427 A | 12/1994 | Stille |
| 5,375,583 A | 12/1994 | Meyer |
| 5,376,123 A | 12/1994 | Klaue |
| 5,380,772 A | 1/1995 | Hasegawa |
| 5,385,081 A | 1/1995 | Sneddon |
| 5,385,566 A | 1/1995 | Ullmark |
| 5,387,191 A | 2/1995 | Hemstreet |
| 5,390,683 A | 2/1995 | Pisharodi |
| 5,395,167 A | 3/1995 | Murray |
| 5,395,326 A | 3/1995 | Haber |
| 5,398,483 A | 3/1995 | Smith |
| 5,401,806 A | 3/1995 | Braden |
| 5,407,266 A | 4/1995 | Dotsch |
| 5,411,180 A | 5/1995 | Dumelle |
| 5,415,474 A | 5/1995 | Nelson |
| 5,423,824 A | 6/1995 | Akerfeldt |
| 5,423,850 A | 6/1995 | Berger |
| 5,431,654 A | 7/1995 | Nic |
| 5,435,645 A | 7/1995 | Faccioli |
| 5,441,502 A | 8/1995 | Bartlett |
| 5,443,182 A | 8/1995 | Tanaka |
| 5,445,631 A | 8/1995 | Uchida |
| 5,445,639 A | 8/1995 | Kuslich |
| 5,448,989 A | 9/1995 | Heckele |
| 5,450,924 A | 9/1995 | Tseng |
| 5,454,365 A | 10/1995 | Bonutti |
| 5,456,267 A | 10/1995 | Stark |
| 5,468,245 A | 11/1995 | Vargas, III |

(56) References Cited

U.S. PATENT DOCUMENTS

| | | |
|---|---|---|
| 5,480,400 A | 1/1996 | Berger |
| 5,480,403 A | 1/1996 | Lee |
| 5,482,187 A | 1/1996 | Poulsen |
| 5,492,247 A | 2/1996 | Shu |
| 5,494,349 A | 2/1996 | Seddon |
| 5,501,374 A | 3/1996 | Laufer |
| 5,501,520 A | 3/1996 | Lidgren |
| 5,501,695 A | 3/1996 | Anspach, Jr. |
| 5,512,610 A | 4/1996 | Lin |
| 5,514,135 A | 5/1996 | Earle |
| 5,514,137 A | 5/1996 | Coutts |
| 5,518,498 A | 5/1996 | Lindenberg |
| 5,520,690 A | 5/1996 | Errico |
| 5,522,816 A | 6/1996 | Dinello |
| 5,522,899 A | 6/1996 | Michelson |
| 5,526,853 A | 6/1996 | McPhee |
| 5,531,519 A | 7/1996 | Earle |
| 5,531,683 A | 7/1996 | Kriesel |
| 5,534,028 A | 7/1996 | Bao |
| 5,536,262 A | 7/1996 | Velasquez |
| 5,545,460 A | 8/1996 | Tanaka |
| 5,548,001 A | 8/1996 | Podszun |
| 5,549,380 A | 8/1996 | Lidgren |
| 5,549,381 A | 8/1996 | Hays |
| 5,549,679 A | 8/1996 | Kuslich |
| 5,551,778 A | 9/1996 | Hauke |
| 5,554,101 A | 9/1996 | Matula |
| 5,556,201 A | 9/1996 | Veltrop |
| 5,558,136 A | 9/1996 | Orrico |
| 5,558,639 A | 9/1996 | Gangemi |
| 5,562,736 A | 10/1996 | Ray |
| 5,571,189 A | 11/1996 | Kuslich |
| 5,573,265 A | 11/1996 | Pradel |
| 5,578,035 A | 11/1996 | Lin |
| 5,586,821 A | 12/1996 | Bonitati |
| 5,588,745 A | 12/1996 | Tanaka |
| 5,591,197 A | 1/1997 | Orth |
| 5,601,557 A | 2/1997 | Hayhurst |
| 5,603,701 A | 2/1997 | Fischer |
| 5,609,637 A | 3/1997 | Biedermann |
| 5,624,184 A | 4/1997 | Chan |
| 5,630,806 A | 5/1997 | Inagaki |
| 5,634,880 A | 6/1997 | Feldman |
| 5,637,097 A | 6/1997 | Yoon |
| 5,638,997 A | 6/1997 | Hawkins |
| 5,641,010 A | 6/1997 | Maier |
| 5,645,598 A | 7/1997 | Brosnahan, III |
| 5,647,856 A | 7/1997 | Eykmann |
| 5,653,686 A | 8/1997 | Coulter |
| 5,658,310 A | 8/1997 | Berger |
| 5,660,186 A | 8/1997 | Bachir |
| 5,665,067 A | 9/1997 | Linder |
| 5,676,699 A | 10/1997 | Gogolewski |
| 5,681,317 A | 10/1997 | Caldarise |
| 5,683,451 A | 11/1997 | Lenker |
| 5,685,826 A | 11/1997 | Bonutti |
| 5,690,606 A | 11/1997 | Slotman |
| 5,690,927 A * | 11/1997 | Major .................... A61K 35/54 424/570 |
| 5,693,100 A | 12/1997 | Pisharodi |
| 5,697,977 A | 12/1997 | Pisharodi |
| 5,698,611 A | 12/1997 | Okada |
| 5,702,448 A | 12/1997 | Buechel |
| 5,704,895 A | 1/1998 | Scott |
| 5,707,390 A | 1/1998 | Bonutti |
| 5,718,707 A | 2/1998 | Mikhail |
| 5,720,753 A | 2/1998 | Sander |
| 5,725,341 A | 3/1998 | Hofmeister |
| 5,725,529 A | 3/1998 | Nicholson |
| 5,747,553 A | 5/1998 | Guzauskas |
| 5,752,935 A | 5/1998 | Robinson |
| 5,752,969 A | 5/1998 | Cunci |
| 5,752,974 A | 5/1998 | Rhee |
| 5,755,732 A | 5/1998 | Green |
| 5,759,186 A | 6/1998 | Bachmann |
| 5,763,092 A | 6/1998 | Lee |
| 5,779,356 A | 7/1998 | Chan |
| 5,782,713 A | 7/1998 | Yang |
| 5,782,747 A | 7/1998 | Zimmon |
| 5,782,830 A | 7/1998 | Farris |
| 5,782,838 A | 7/1998 | Beyar |
| 5,785,647 A | 7/1998 | Tompkins |
| 5,785,682 A | 7/1998 | Grabenkort |
| 5,792,044 A | 8/1998 | Foley |
| 5,795,922 A | 8/1998 | Demian |
| 5,797,678 A | 8/1998 | Murray |
| 5,800,169 A | 9/1998 | Muhlbauer |
| 5,800,409 A | 9/1998 | Bruce |
| 5,800,549 A | 9/1998 | Bao |
| 5,800,550 A | 9/1998 | Sertich |
| 5,810,885 A | 9/1998 | Zinger |
| 5,820,321 A | 10/1998 | Gruber |
| 5,824,087 A | 10/1998 | Aspden |
| 5,826,713 A | 10/1998 | Sunago |
| 5,826,753 A | 10/1998 | Fehlig |
| 5,827,217 A | 10/1998 | Silver |
| 5,827,289 A | 10/1998 | Reiley |
| 5,829,875 A | 11/1998 | Hagel |
| 5,830,194 A | 11/1998 | Anwar |
| 5,836,306 A | 11/1998 | Duane |
| 5,836,914 A | 11/1998 | Houghton |
| 5,839,621 A | 11/1998 | Tada |
| 5,842,785 A | 12/1998 | Brown |
| 5,842,786 A | 12/1998 | Dover |
| 5,865,802 A | 2/1999 | Yoon |
| 5,868,782 A | 2/1999 | Frantzen |
| 5,876,116 A | 3/1999 | Barker |
| 5,876,457 A | 3/1999 | Picha |
| 5,882,340 A | 3/1999 | Yoon |
| 5,884,818 A | 3/1999 | Campbell |
| 5,887,755 A * | 3/1999 | Hood, III ......... A61B 17/00491 222/135 |
| 5,893,488 A | 4/1999 | Hoag |
| 5,893,850 A | 4/1999 | Cachia |
| 5,902,839 A | 5/1999 | Lautenschlager |
| 5,911,721 A | 6/1999 | Nicholson |
| 5,918,702 A | 7/1999 | Cheng |
| 5,918,770 A | 7/1999 | Camm |
| 5,925,051 A | 7/1999 | Mikhail |
| 5,928,239 A | 7/1999 | Mirza |
| 5,931,347 A | 8/1999 | Haubrich |
| 5,941,851 A | 8/1999 | Coffey |
| 5,954,671 A | 9/1999 | O'Neill |
| 5,954,728 A | 9/1999 | Heller |
| 5,961,211 A | 10/1999 | Barker |
| 5,968,008 A | 10/1999 | Grams |
| 5,968,044 A | 10/1999 | Nicholson |
| 5,968,999 A | 10/1999 | Ramp |
| 5,972,015 A | 10/1999 | Scribner |
| 5,980,527 A | 11/1999 | Cohen |
| 5,989,290 A | 11/1999 | Biedermann |
| 5,993,535 A | 11/1999 | Sawamura |
| 5,997,544 A | 12/1999 | Nies |
| 6,004,325 A | 12/1999 | Vargas, III |
| 6,007,496 A | 12/1999 | Brannon |
| 6,017,349 A | 1/2000 | Heller |
| 6,019,765 A | 2/2000 | Thornhill |
| 6,019,776 A | 2/2000 | Preissman |
| 6,019,789 A | 2/2000 | Dinh |
| 6,020,396 A | 2/2000 | Jacobs |
| 6,022,339 A | 2/2000 | Fowles |
| 6,025,537 A | 2/2000 | Werding |
| 6,033,105 A | 3/2000 | Barker |
| 6,033,411 A | 3/2000 | Preissman |
| 6,039,761 A | 3/2000 | Li |
| 6,040,408 A | 3/2000 | Koole |
| 6,041,977 A | 3/2000 | Lisi |
| 6,042,262 A | 3/2000 | Hajianpour |
| 6,045,555 A | 4/2000 | Smith |
| 6,048,346 A | 4/2000 | Reiley |
| 6,049,026 A | 4/2000 | Muschler |
| 60,455,555 | 4/2000 | Smith |
| 6,075,067 A | 6/2000 | Lidgren |
| 6,077,265 A | 6/2000 | Werding |

(56) References Cited

U.S. PATENT DOCUMENTS

| | | | |
|---|---|---|---|
| 6,080,579 A | 6/2000 | Hanley, Jr. | |
| 6,080,801 A | 6/2000 | Draenert | |
| 6,080,811 A | 6/2000 | Schehlmann | |
| 6,083,229 A | 7/2000 | Constantz | |
| 6,086,594 A | 7/2000 | Brown | |
| 6,103,779 A | 8/2000 | Guzauskas | |
| 6,116,773 A | 9/2000 | Murray | |
| 6,120,174 A | 9/2000 | Hoag | |
| 6,124,373 A | 9/2000 | Peter | |
| 6,126,689 A | 10/2000 | Brett | |
| 6,127,597 A | 10/2000 | Beyar | |
| 6,129,763 A | 10/2000 | Chauvin | |
| 6,132,396 A | 10/2000 | Antanavich | |
| 6,136,038 A | 10/2000 | Raab | |
| 6,139,509 A | 10/2000 | Yuan | |
| 6,142,998 A | 11/2000 | Smith | |
| 6,146,401 A | 11/2000 | Yoon | |
| 6,149,651 A | 11/2000 | Drewry | |
| 6,149,655 A | 11/2000 | Constantz | |
| 6,149,664 A | 11/2000 | Kurz | |
| 6,160,033 A | 12/2000 | Nies | |
| 6,161,955 A | 12/2000 | Rademaker | |
| 6,168,597 B1 | 1/2001 | Biedermann | |
| 6,174,935 B1 | 1/2001 | Matsunae | |
| 6,176,607 B1 | 1/2001 | Hajianpour | |
| 6,183,441 B1 | 2/2001 | Kriesel | |
| 6,183,516 B1 | 2/2001 | Burkinshaw | |
| 6,187,015 B1 | 2/2001 | Brenneman | |
| 6,190,381 B1 | 2/2001 | Olsen | |
| 6,200,289 B1 * | 3/2001 | Hochman | A61M 5/1456 128/DIG. 12 |
| 6,206,058 B1 | 3/2001 | Nagel | |
| 6,210,031 B1 | 4/2001 | Murray | |
| 6,214,012 B1 | 4/2001 | Karpman | |
| 6,214,016 B1 | 4/2001 | Williams | |
| 6,214,037 B1 | 4/2001 | Mitchell | |
| 6,217,566 B1 | 4/2001 | Ju | |
| 6,217,581 B1 | 4/2001 | Tolson | |
| 6,217,608 B1 | 4/2001 | Penn | |
| 6,221,029 B1 | 4/2001 | Mathis | |
| 6,224,604 B1 | 5/2001 | Suddaby | |
| 6,228,049 B1 | 5/2001 | Schroeder | |
| 6,228,068 B1 | 5/2001 | Yoon | |
| 6,228,082 B1 | 5/2001 | Baker | |
| 6,231,615 B1 | 5/2001 | Preissman | |
| 6,235,043 B1 | 5/2001 | Reiley | |
| 6,238,399 B1 | 5/2001 | Heller | |
| 6,241,734 B1 | 6/2001 | Scribner | |
| 6,245,101 B1 | 6/2001 | Drasler | |
| 6,248,110 B1 | 6/2001 | Reiley | |
| 6,254,268 B1 | 7/2001 | Long | |
| 6,261,289 B1 | 7/2001 | Levy | |
| 6,264,618 B1 | 7/2001 | Landi | |
| 6,264,659 B1 | 7/2001 | Ross | |
| 6,264,660 B1 | 7/2001 | Schmidt | |
| 6,273,916 B1 | 8/2001 | Murphy | |
| 6,281,271 B1 | 8/2001 | Rumphorst | |
| 6,309,395 B1 | 10/2001 | Smith | |
| 6,309,420 B1 | 10/2001 | Preissman | |
| 6,312,149 B1 | 11/2001 | Sjövall | |
| 6,325,812 B1 | 12/2001 | Dubrul | |
| 6,348,055 B1 | 2/2002 | Preissman | |
| 6,348,518 B1 | 2/2002 | Montgomery | |
| 6,350,271 B1 | 2/2002 | Kurz | |
| 6,361,539 B1 | 3/2002 | Heller | |
| 6,364,865 B1 | 4/2002 | Lavi | |
| 6,367,962 B1 | 4/2002 | Mizutani | |
| 6,375,659 B1 | 4/2002 | Erbe | |
| 6,375,682 B1 | 4/2002 | Fleischmann | |
| 6,383,188 B2 | 5/2002 | Kuslich | |
| 6,383,190 B1 | 5/2002 | Preissman | |
| 6,395,007 B1 | 5/2002 | Bhatnagar | |
| 6,402,701 B1 | 6/2002 | Kaplan | |
| 6,402,758 B1 | 6/2002 | Tolson | |
| 6,406,175 B1 | 6/2002 | Marino | |
| 6,409,972 B1 | 6/2002 | Chan | |
| 6,410,612 B1 | 6/2002 | Hatanaka | |
| 6,425,885 B1 | 7/2002 | Fischer | |
| 6,425,887 B1 | 7/2002 | McGuckin | |
| 6,431,743 B1 | 8/2002 | Mizutani | |
| 6,433,037 B1 | 8/2002 | Guzauskas | |
| 6,436,143 B1 | 8/2002 | Ross | |
| 6,439,439 B1 | 8/2002 | Rickard | |
| 6,443,334 B1 | 9/2002 | John | |
| 6,447,478 B1 | 9/2002 | Maynard | |
| 6,450,973 B1 | 9/2002 | Murphy | |
| 6,458,117 B1 | 10/2002 | Pollins, Sr. | |
| 6,479,565 B1 | 11/2002 | Stanley | |
| 6,485,465 B2 * | 11/2002 | Moberg | A61M 5/1456 417/18 |
| 6,488,667 B1 | 12/2002 | Murphy | |
| 6,494,868 B2 | 12/2002 | Amar | |
| 6,500,182 B2 | 12/2002 | Foster | |
| 6,502,608 B1 | 1/2003 | Burchett | |
| 6,527,144 B2 | 3/2003 | Ritsche | |
| 6,533,807 B2 | 3/2003 | Wolinsky | |
| 6,550,957 B2 | 4/2003 | Mizutani | |
| 6,554,833 B2 | 4/2003 | Levy | |
| 6,568,439 B1 | 5/2003 | Se | |
| 6,572,256 B2 | 6/2003 | Seaton | |
| 6,575,331 B1 | 6/2003 | Peeler | |
| 6,575,919 B1 | 6/2003 | Reiley | |
| 6,582,439 B1 | 6/2003 | Sproul | |
| 6,582,446 B1 | 6/2003 | Marchosky | |
| 6,592,559 B1 | 7/2003 | Pakter | |
| 6,592,624 B1 | 7/2003 | Fraser | |
| 6,595,967 B2 | 7/2003 | Kramer | |
| 6,599,293 B2 | 7/2003 | Tague | |
| 6,599,520 B2 | 7/2003 | Scarborough | |
| 6,604,003 B2 | 8/2003 | Fredricks | |
| 6,613,018 B2 | 9/2003 | Bagga | |
| 6,613,054 B2 | 9/2003 | Scribner | |
| 6,613,079 B1 | 9/2003 | Wolinsky | |
| 6,620,169 B1 | 9/2003 | Peterson | |
| 6,626,912 B2 | 9/2003 | Speitling | |
| 6,638,300 B1 | 10/2003 | Frantzen | |
| 6,641,587 B2 | 11/2003 | Scribner | |
| 6,645,213 B2 | 11/2003 | Sand | |
| 6,662,969 B2 | 12/2003 | Peeler | |
| 6,676,664 B1 | 1/2004 | Al-Assir | |
| 6,689,823 B1 | 2/2004 | Bellare | |
| 6,702,455 B2 | 3/2004 | Vendrely | |
| 6,712,853 B2 | 3/2004 | Kuslich | |
| 6,716,216 B1 | 4/2004 | Boucher | |
| 6,719,761 B1 | 4/2004 | Reiley | |
| 6,720,417 B1 | 4/2004 | Walter | |
| 6,730,095 B2 | 5/2004 | Olson, Jr. | |
| 6,752,180 B2 | 6/2004 | Delay | |
| 6,758,837 B2 | 7/2004 | Péclat | |
| 6,759,449 B2 | 7/2004 | Kimura | |
| 6,767,973 B2 | 7/2004 | Suau | |
| 6,768,279 B1 | 7/2004 | Skinner | |
| 6,770,079 B2 | 8/2004 | Bhatnagar | |
| 6,779,566 B2 | 8/2004 | Engel | |
| 6,780,175 B1 | 8/2004 | Sachdeva | |
| 6,783,515 B1 | 8/2004 | Miller | |
| 6,787,584 B2 | 9/2004 | Jia | |
| 6,793,660 B2 | 9/2004 | Kerr | |
| 6,796,987 B2 | 9/2004 | Tague | |
| 6,852,095 B1 | 2/2005 | Ray | |
| 6,852,439 B2 | 2/2005 | Frank | |
| 6,874,927 B2 | 4/2005 | Foster | |
| 6,875,219 B2 | 4/2005 | Arramon | |
| 6,887,246 B2 | 5/2005 | Bhatnagar | |
| 6,916,308 B2 | 7/2005 | Dixon | |
| 6,954,949 B1 | 10/2005 | Chen | |
| 6,957,747 B2 | 10/2005 | Peeler | |
| 6,974,247 B2 | 12/2005 | Frei | |
| 6,974,416 B2 | 12/2005 | Booker | |
| 6,979,341 B2 | 12/2005 | Scribner | |
| 6,979,352 B2 | 12/2005 | Reynolds | |
| 6,980,862 B2 | 12/2005 | Fredricks | |
| 6,994,465 B2 | 2/2006 | Tague | |
| 6,997,930 B1 | 2/2006 | Jäggi | |

(56) References Cited

U.S. PATENT DOCUMENTS

| | | |
|---|---|---|
| 7,008,433 B2 | 3/2006 | Voellmicke |
| 7,025,771 B2 | 4/2006 | Kuslich |
| 7,029,163 B2 | 4/2006 | Barker |
| 7,044,937 B1 | 5/2006 | Kirwan |
| 7,044,954 B2 | 5/2006 | Reiley |
| 7,048,743 B2 | 5/2006 | Miller |
| 7,063,703 B2 | 6/2006 | Reo |
| 7,066,942 B2 | 6/2006 | Treace |
| 7,087,040 B2 | 8/2006 | McGuckin, Jr. |
| 7,091,258 B2 | 8/2006 | Neubert |
| 7,097,648 B1 | 8/2006 | Globerman |
| 7,112,205 B2 | 9/2006 | Carrison |
| 7,116,121 B1 | 10/2006 | Holcombe |
| 7,138,442 B2 | 11/2006 | Smith |
| 7,186,761 B2 | 3/2007 | Soffiati |
| 7,189,240 B1 | 3/2007 | Dekel |
| 7,252,671 B2 | 8/2007 | Scribner |
| 7,264,622 B2 | 9/2007 | Michelson |
| 7,270,667 B2 | 9/2007 | Faccioli |
| 7,278,778 B2 | 10/2007 | Sand |
| 7,320,540 B2 | 1/2008 | Coffeen |
| 7,326,203 B2 | 2/2008 | Papineau |
| 7,456,024 B2 | 11/2008 | Dahm |
| 7,470,258 B2 | 12/2008 | Barker |
| 7,510,579 B2 | 3/2009 | Preissman |
| 7,559,932 B2 | 7/2009 | Truckai |
| 7,566,320 B2 | 7/2009 | Duchon |
| 7,572,263 B2 | 8/2009 | Preissman |
| 7,575,577 B2 | 8/2009 | Boyd |
| 7,604,618 B2 | 10/2009 | Dixon |
| 7,621,950 B1 | 11/2009 | Globerman |
| 7,645,066 B2 | 1/2010 | Tague |
| 7,666,205 B2 | 2/2010 | Weikel |
| 7,678,116 B2 | 3/2010 | Truckai |
| 7,693,567 B2 | 4/2010 | Tsonton |
| 7,702,397 B2 | 4/2010 | Fredricks |
| 7,708,751 B2 | 5/2010 | Hughes |
| 7,711,407 B2 | 5/2010 | Hughes |
| 7,717,918 B2 | 5/2010 | Truckai |
| 7,722,612 B2 | 5/2010 | Sala |
| 7,722,620 B2 | 5/2010 | Truckai |
| 7,831,290 B2 | 11/2010 | Hughes |
| 7,841,763 B2 | 11/2010 | Foster |
| 7,862,517 B2 | 1/2011 | Tsonton |
| 7,967,499 B2 | 6/2011 | Tague |
| 8,038,682 B2 | 10/2011 | McGill |
| 8,066,713 B2 | 11/2011 | DiMauro |
| 8,070,753 B2 | 12/2011 | Truckai |
| 8,079,999 B2 | 12/2011 | Duchon |
| 8,128,276 B2 | 3/2012 | Axelsson |
| 8,333,773 B2 | 12/2012 | DiMauro |
| 8,360,629 B2 | 1/2013 | Globerman |
| 8,361,078 B2 | 1/2013 | Beyar |
| 8,415,407 B2 | 4/2013 | Beyar |
| 8,540,722 B2 | 9/2013 | Beyar |
| 8,579,908 B2 | 11/2013 | Mazzuca |
| 8,809,418 B2 | 8/2014 | Beyar |
| 8,950,929 B2 | 2/2015 | Globerman |
| 8,956,368 B2 | 2/2015 | Beyar |
| 9,186,194 B2 | 11/2015 | Ferreyro |
| 9,259,696 B2 | 2/2016 | Globerman |
| 9,381,024 B2 | 7/2016 | Globerman |
| 9,504,508 B2 | 11/2016 | Beyar |
| 9,642,932 B2 | 5/2017 | Beyar |
| 9,750,840 B2 | 9/2017 | Beyar |
| 9,839,460 B2 | 12/2017 | DiMauro |
| 9,918,767 B2 | 3/2018 | Globerman |
| 2001/0012968 A1 | 8/2001 | Preissman |
| 2001/0024400 A1 | 9/2001 | Van Der Wel |
| 2001/0031975 A1* | 10/2001 | Whitman ........... A61B 10/0233 606/167 |
| 2001/0034527 A1 | 10/2001 | Scribner |
| 2002/0008122 A1 | 1/2002 | Ritsche |
| 2002/0010431 A1 | 1/2002 | Dixon |
| 2002/0010471 A1 | 1/2002 | Wironen |
| 2002/0010472 A1 | 1/2002 | Kuslich |
| 2002/0013553 A1 | 1/2002 | Pajunk |
| 2002/0049448 A1 | 4/2002 | Sand |
| 2002/0049449 A1 | 4/2002 | Bhatnagar |
| 2002/0058947 A1 | 5/2002 | Hochschuler |
| 2002/0067658 A1 | 6/2002 | Vendrely |
| 2002/0068939 A1 | 6/2002 | Levy |
| 2002/0068974 A1 | 6/2002 | Kuslich |
| 2002/0068975 A1 | 6/2002 | Teitelbaum |
| 2002/0072768 A1 | 6/2002 | Ginn |
| 2002/0082605 A1 | 6/2002 | Reiley |
| 2002/0088131 A1 | 7/2002 | Baxa |
| 2002/0099384 A1 | 7/2002 | Scribner |
| 2002/0099385 A1 | 7/2002 | Ralph |
| 2002/0118595 A1 | 8/2002 | Miller |
| 2002/0123716 A1 | 9/2002 | VanDiver |
| 2002/0156483 A1 | 10/2002 | Voellmicke |
| 2002/0161373 A1 | 10/2002 | Osorio |
| 2002/0177866 A1 | 11/2002 | Weikel |
| 2002/0183851 A1 | 12/2002 | Spiegelberg |
| 2002/0188300 A1 | 12/2002 | Arramon |
| 2002/0191487 A1 | 12/2002 | Sand |
| 2003/0009177 A1 | 1/2003 | Middleman |
| 2003/0018339 A1 | 1/2003 | Higueras |
| 2003/0031698 A1 | 2/2003 | Roeder |
| 2003/0032929 A1 | 2/2003 | McGuckin |
| 2003/0032964 A1 | 2/2003 | Watkins |
| 2003/0036762 A1 | 2/2003 | Kerr |
| 2003/0036763 A1 | 2/2003 | Bhatnagar |
| 2003/0040718 A1 | 2/2003 | Kust |
| 2003/0050644 A1 | 3/2003 | Boucher |
| 2003/0050702 A1 | 3/2003 | Berger |
| 2003/0078589 A1 | 4/2003 | Preissman |
| 2003/0109883 A1 | 6/2003 | Matsuzaki |
| 2003/0109884 A1 | 6/2003 | Tague |
| 2003/0144742 A1 | 7/2003 | King |
| 2003/0162864 A1 | 8/2003 | Pearson |
| 2003/0174576 A1 | 9/2003 | Tague |
| 2003/0181963 A1 | 9/2003 | Pellegrino |
| 2003/0185093 A1 | 10/2003 | Vendrely |
| 2003/0220414 A1 | 11/2003 | Axen |
| 2003/0225364 A1 | 12/2003 | Kraft |
| 2003/0227816 A1 | 12/2003 | Okamoto |
| 2003/0231545 A1 | 12/2003 | Seaton |
| 2004/0006348 A1 | 1/2004 | Peterson |
| 2004/0010263 A1 | 1/2004 | Boucher |
| 2004/0029996 A1 | 2/2004 | Kuhn |
| 2004/0033124 A1 | 2/2004 | Schaeff |
| 2004/0044096 A1 | 3/2004 | Smith |
| 2004/0054377 A1 | 3/2004 | Foster |
| 2004/0066706 A1 | 4/2004 | Barker |
| 2004/0068264 A1 | 4/2004 | Treace |
| 2004/0073139 A1 | 4/2004 | Hirsch |
| 2004/0092946 A1 | 5/2004 | Bagga |
| 2004/0098015 A1 | 5/2004 | Weikel |
| 2004/0133124 A1 | 7/2004 | Bates |
| 2004/0133211 A1 | 7/2004 | Raskin |
| 2004/0162559 A1 | 8/2004 | Arramon |
| 2004/0167532 A1 | 8/2004 | Olson |
| 2004/0167562 A1 | 8/2004 | Osorio |
| 2004/0215202 A1 | 10/2004 | Preissman |
| 2004/0230309 A1 | 11/2004 | DiMauro |
| 2004/0249347 A1 | 12/2004 | Miller |
| 2004/0260304 A1 | 12/2004 | Faccioli |
| 2004/0267154 A1 | 12/2004 | Sutton |
| 2005/0008528 A1 | 1/2005 | Prabhu |
| 2005/0014273 A1 | 1/2005 | Dahm |
| 2005/0015148 A1 | 1/2005 | Jansen |
| 2005/0025622 A1 | 2/2005 | Djeridane |
| 2005/0058717 A1 | 3/2005 | Yetkinler |
| 2005/0060023 A1 | 3/2005 | Mitchell |
| 2005/0069397 A1 | 3/2005 | Shavit |
| 2005/0070912 A1 | 3/2005 | Voellmicke |
| 2005/0070914 A1 | 3/2005 | Constantz |
| 2005/0070915 A1 | 3/2005 | Mazzuca |
| 2005/0083782 A1 | 4/2005 | Gronau |
| 2005/0113762 A1 | 5/2005 | Kay |
| 2005/0143827 A1 | 6/2005 | Globerman |
| 2005/0154081 A1 | 7/2005 | Yin |

(56) References Cited

U.S. PATENT DOCUMENTS

| | | |
|---|---|---|
| 2005/0157588 A1 | 7/2005 | Jonsson |
| 2005/0159724 A1 | 7/2005 | Enerson |
| 2005/0180806 A1 | 8/2005 | Green |
| 2005/0203206 A1 | 9/2005 | Trieu |
| 2005/0209695 A1 | 9/2005 | de Vries |
| 2005/0216025 A1 | 9/2005 | Chern Lin |
| 2005/0256220 A1 | 11/2005 | Lavergne |
| 2005/0261625 A1 | 11/2005 | Ashman |
| 2005/0281132 A1 | 12/2005 | Armstrong |
| 2006/0035997 A1 | 2/2006 | Orlowski |
| 2006/0041033 A1 | 2/2006 | Bisig |
| 2006/0052794 A1 | 3/2006 | McGill |
| 2006/0074433 A1 | 4/2006 | McGill |
| 2006/0079905 A1 | 4/2006 | Beyar |
| 2006/0085008 A1 | 4/2006 | Jaggi |
| 2006/0116643 A1 | 6/2006 | Dixon |
| 2006/0116689 A1 | 6/2006 | Albans |
| 2006/0116690 A1 | 6/2006 | Pagano |
| 2006/0122614 A1 | 6/2006 | Truckai |
| 2006/0148923 A1 | 7/2006 | Ashman |
| 2006/0164913 A1 | 7/2006 | Arramon |
| 2006/0167148 A1 | 7/2006 | Engqvist |
| 2006/0181959 A1 | 8/2006 | Weiss |
| 2006/0235338 A1 | 10/2006 | Pacheco |
| 2006/0235417 A1 | 10/2006 | Sala |
| 2006/0241606 A1 | 10/2006 | Vachtenberg |
| 2006/0241644 A1 | 10/2006 | Osorio |
| 2006/0264695 A1 | 11/2006 | Viole |
| 2006/0264967 A1 | 11/2006 | Ferreyro |
| 2006/0266372 A1 | 11/2006 | Miller |
| 2006/0271061 A1 | 11/2006 | Beyar |
| 2006/0276819 A1 | 12/2006 | Osorio |
| 2007/0019802 A1 | 1/2007 | Ubriaco |
| 2007/0027230 A1 | 2/2007 | Beyar |
| 2007/0032567 A1 | 2/2007 | Beyar |
| 2007/0043373 A1 | 2/2007 | Sala |
| 2007/0055266 A1 | 3/2007 | Osorio |
| 2007/0055267 A1 | 3/2007 | Osorio |
| 2007/0055278 A1 | 3/2007 | Osorio |
| 2007/0055280 A1 | 3/2007 | Osorio |
| 2007/0055284 A1 | 3/2007 | Osorio |
| 2007/0055285 A1 | 3/2007 | Osorio |
| 2007/0055300 A1 | 3/2007 | Osorio |
| 2007/0060941 A1 | 3/2007 | Reiley |
| 2007/0118142 A1 | 5/2007 | Krueger |
| 2007/0121422 A1 | 5/2007 | Sand |
| 2007/0142842 A1 | 6/2007 | Krueger |
| 2007/0162042 A1 | 7/2007 | Dunker |
| 2007/0197935 A1 | 8/2007 | Reiley |
| 2007/0198013 A1 | 8/2007 | Foley |
| 2007/0198023 A1 | 8/2007 | Sand |
| 2007/0198024 A1 | 8/2007 | Plishka |
| 2007/0255282 A1 | 11/2007 | Simonton |
| 2007/0282443 A1 | 12/2007 | Globerman |
| 2008/0039856 A1 | 2/2008 | DiMauro |
| 2008/0044374 A1 | 2/2008 | Lavergne |
| 2008/0058827 A1 | 3/2008 | Osorio |
| 2008/0065087 A1 | 3/2008 | Osorio |
| 2008/0065089 A1 | 3/2008 | Osorio |
| 2008/0065137 A1 | 3/2008 | Boucher |
| 2008/0065142 A1 | 3/2008 | Reiley |
| 2008/0065190 A1 | 3/2008 | Osorio |
| 2008/0071283 A1 | 3/2008 | Osorio |
| 2008/0086133 A1 | 4/2008 | Kuslich |
| 2008/0132935 A1 | 6/2008 | Osorio |
| 2008/0140079 A1 | 6/2008 | Osorio |
| 2008/0140084 A1 | 6/2008 | Osorio |
| 2008/0200915 A1 | 8/2008 | Globerman |
| 2008/0212405 A1 | 9/2008 | Globerman |
| 2008/0228192 A1 | 9/2008 | Beyar |
| 2008/0300536 A1 | 12/2008 | Wang |
| 2008/0319445 A9 | 12/2008 | McGill |
| 2009/0264892 A1 | 10/2009 | Beyar |
| 2009/0264942 A1 | 10/2009 | Beyar |
| 2009/0270872 A1 | 10/2009 | DiMauro |
| 2010/0065154 A1 | 3/2010 | Globerman |
| 2010/0069786 A1 | 3/2010 | Globerman |
| 2010/0152855 A1 | 6/2010 | Kuslich |
| 2010/0168271 A1 | 7/2010 | Beyar |
| 2010/0268231 A1 | 10/2010 | Kuslich |
| 2010/0274243 A1 | 10/2010 | Fredricks |
| 2012/0307586 A1 | 12/2012 | Globerman |
| 2013/0123791 A1 | 5/2013 | Beyar |
| 2013/0261217 A1 | 10/2013 | Beyar |
| 2013/0345708 A1 | 12/2013 | Beyar |
| 2014/0088605 A1 | 3/2014 | Ferreyro |
| 2014/0148866 A1 | 5/2014 | Globerman |
| 2015/0122691 A1 | 5/2015 | Globerman |
| 2015/0127058 A1 | 5/2015 | Beyar |
| 2015/0148777 A1 | 5/2015 | Ferreyro |
| 2016/0051302 A1 | 2/2016 | Ferreyro |
| 2016/0235459 A1 | 8/2016 | Globerman |
| 2017/0216483 A1 | 8/2017 | Beyar |

FOREIGN PATENT DOCUMENTS

| | | |
|---|---|---|
| DE | 136018 | 12/1901 |
| DE | 226956 | 3/1909 |
| DE | 868497 | 2/1953 |
| DE | 1283448 | 11/1968 |
| DE | 1810799 | 6/1970 |
| DE | 2821785 | 11/1979 |
| DE | 3003947 | 8/1980 |
| DE | 2947875 | 6/1981 |
| DE | 3443167 | 6/1986 |
| DE | 8716073 | 3/1988 |
| DE | 3817101 | 11/1989 |
| DE | 4104092 | 8/1991 |
| DE | 293485 | 9/1991 |
| DE | 19612276 | 10/1997 |
| DE | 10258140 | 12/2005 |
| EP | 0044877 | 3/1985 |
| EP | 0 235 905 | 9/1987 |
| EP | 0 235 905 | 12/1990 |
| EP | 235905 | 12/1990 |
| EP | 0 614 653 | 9/1994 |
| EP | 1 074 231 | 2/2001 |
| EP | 1 095 667 | 5/2001 |
| EP | 1095667 | 5/2001 |
| EP | 1 104 260 | 6/2001 |
| EP | 1 247 454 | 10/2002 |
| EP | 1 517 655 | 3/2005 |
| EP | 1 596 896 | 11/2005 |
| EP | 1 598 015 | 11/2005 |
| EP | 1104260 | 8/2006 |
| EP | 1 829 518 | 9/2007 |
| EP | 1 886 647 | 2/2008 |
| EP | 1 886 648 | 2/2008 |
| EP | 1829518 | 8/2009 |
| EP | 1886647 | 4/2011 |
| EP | 0614653 | 8/2011 |
| FR | 1548575 | 12/1968 |
| FR | 2606282 | 5/1988 |
| FR | 2629337 | 10/1989 |
| FR | 2638972 | 5/1990 |
| FR | 2674119 | 9/1992 |
| FR | 2690332 | 10/1993 |
| FR | 2712486 | 5/1995 |
| FR | 2722679 | 1/1996 |
| GB | 179502045 | 4/1795 |
| GB | 8331 | 3/1904 |
| GB | 190720207 | 6/1908 |
| GB | 408668 | 4/1934 |
| GB | 486638 | 6/1938 |
| GB | 2114005 | 8/1983 |
| GB | 2197691 | 5/1988 |
| GB | 2268068 | 1/1994 |
| GB | 2441849 | 9/2005 |
| GB | 2469749 | 10/2010 |
| JP | 51-134465 | 11/1976 |
| JP | 54009110 | 1/1979 |
| JP | 55-009242 | 1/1980 |
| JP | 55-109440 | 8/1980 |
| JP | 55109440 | 8/1980 |

(56) References Cited

FOREIGN PATENT DOCUMENTS

| | | |
|---|---|---|
| JP | 62068893 | 3/1987 |
| JP | 62-068893 U1 | 4/1987 |
| JP | 63-194722 | 8/1988 |
| JP | 2122017 | 5/1990 |
| JP | 2166235 | 6/1990 |
| JP | 04-329956 | 11/1992 |
| JP | 4329956 | 11/1992 |
| JP | 05034760 | 9/1993 |
| JP | 07-000410 | 1/1995 |
| JP | 8322848 | 12/1996 |
| JP | 10146559 | 6/1998 |
| JP | 10-511569 | 10/1998 |
| JP | 2001- 514922 | 9/2001 |
| JP | 2004-016707 | 1/2004 |
| JP | 2004016707 | 1/2004 |
| JP | 2005- 500103 | 1/2005 |
| JP | 2008055367 | 3/2008 |
| RO | 116784 | 6/2001 |
| RU | 662082 | 5/1979 |
| RU | 1011119 | 4/1983 |
| RU | 1049050 | 10/1983 |
| WO | WO 88/10129 | 12/1988 |
| WO | WO 1990000037 | 1/1990 |
| WO | WO 1994012112 | 6/1994 |
| WO | WO 1994/26213 | 11/1994 |
| WO | WO 1994026213 | 11/1994 |
| WO | WO 1997018769 | 5/1997 |
| WO | WO 97/28835 | 8/1997 |
| WO | WO 1997028835 | 8/1997 |
| WO | WO 1998038918 | 9/1998 |
| WO | WO 1999029253 | 6/1999 |
| WO | WO 1999052446 | 3/2000 |
| WO | WO 2000044321 | 12/2000 |
| WO | WO 2001060270 | 8/2001 |
| WO | WO 02/19933 | 3/2002 |
| WO | WO 2002019933 | 3/2002 |
| WO | WO 2001076514 | 5/2002 |
| WO | WO 02/064195 | 8/2002 |
| WO | WO 2003007854 | 1/2003 |
| WO | WO 2002000143 | 2/2003 |
| WO | WO 2002100143 | 2/2003 |
| WO | WO 03/022165 | 3/2003 |
| WO | WO 2003022165 | 3/2003 |
| WO | WO 03/078041 | 9/2003 |
| WO | WO 2003078041 | 9/2003 |
| WO | WO 2004/080357 | 9/2004 |
| WO | WO 2004/110292 | 12/2004 |
| WO | WO 2005/000138 | 1/2005 |
| WO | WO 2005/017000 | 2/2005 |
| WO | WO 2004110300 | 6/2005 |
| WO | WO 2005032326 | 6/2005 |
| WO | WO 2005048867 | 8/2005 |
| WO | WO 2006/062939 | 6/2006 |
| WO | WO 2006090379 | 11/2006 |
| WO | WO 2006011152 | 5/2007 |
| WO | WO 2007036815 | 9/2007 |
| WO | WO 2007015202 | 11/2007 |

OTHER PUBLICATIONS

Edeland, "Some additional suggestions for an intervertebral disc prothesis," J. Biomed. Eng. XP008072822, 7(1):57-62 (1985.
Farrar, D.F. et al., "Rheological Properties of PMMA Bone Cements During Curing," Biomaterials 22:3005-13 (2001).
Feldman, H. "Die Geschichte der Injektionen " Laryngo-Rhino-Othol 79:239-46 (2000).
Fessler, Richard D. et al., "Vertebroplasty," Neurosurgical Operative Atlas 9:233-240 (2000).
Gangi, A., "Computed Tomography Ct and Fluoroscopy-Guided Vertebroplasty: Results and Complications in 187 Patients," Seminars in Interventional Radiology 16(2):137-42 (1999).
Gangi, A., "CT-Guided Interventional Procedures for Pain Management in the Lumbosacral Spine," Radiographics 18:621-633 (1998).
Gangi, A., "Percutaneous Vertebroplasty Guided by a Combination of CT and Fluroscopy" AINR 15:83-86 (1994).
Garfin, S. R. et al., "New Technologies in Spine, Kyphoplasty and Vertebroplasty for the Treatment of Painful Osteoporotic Compression Fractures," Spine 26(14:1511-15 (2001).
Gheduzzi, S. et al., "Mechanical Characterisation of Three Percutaneous Vertebroplasty Biomaterials," J. Mater Sci Mater Med 17(5):421-26 (2006).
Giannitsios, D. et al., "High Cement Viscosity Reduces Leakage Risk in Vertebroplasty," European Cells & Mat. 10 supp. 3:54 (2005).
Glasgow Medico-Chirurgical Society, The lancet 1364 (May 18, 1907).
Odian, G., "Principles of Polymerization," pp. 20-23.
Padovani, B. et al., "Pulmonary Embolism Caused by Acrylic Cement: A Rare Complication of Percutaneous Vertebroplasty," AJNR 20:375-77 (1999).
Paget, S., "The Uses of Paraffin in Plastic Surgery," The Lancet 1354 (May 16, 1903).
Parallax Medical, Inc., Exflow Cement Delivery System (May 16, 2000).
Pascual, B. et al., "New Aspects of the Effect of Size and Size Distribution on the Setting Parameters and Mechanical Properties of Acrylic Bone Cements," Biomaterials 17(5):509-16 (1996).
Rimnac, CM, et al., "The effect of centrifugation on the fracture properties of acrylic bone cements," JB&JS 68A(2):281-87 (1986).
Robinson, R. et al., "Mechanical Properties of Poly(methyl methacrylate) Bone Cement," J. Biomed. Materials Res. 15(2):203-08 (2004).
Ryu, K. S. et al., "Dose-Dependent Epidural Leakage of Polymethylmethacrylate after Percutaneous Vertebroplasty in Pateints with Osteoporotic Vertebral Compression Fractures," J. Neuro: Spine 96:56-61 (2002).
Saha, S. et al., "Mechanical Properties of Bone Cement: A Review," J. Biomed. Materials Res. 18(4):435-62 (1984).
Serbetci, K. et al., "Thermal and Mechanical Properties of Hydroxyapatite Impregnated Acrylic Bone Cements," Polymer Testing 23:145-55 (2004).
Shah, T., Radiopaque Polymer Formulations for Medical Devices; Medical Plastics and Biomaterials Special Section; Medical device & Diagnostic Industry pp. 102-111 (2000).
Steen, "Laser Surface Treatment," Laser Mat. Processing, Springer 2d ed. ch. 6:218-71 (2003).
Al-Assir, et al., "Percutaneous Vertebroplasty: A Special Syringe for Cement Injection," AJNR Am. J. Neuroradiol. 21:159-61 (Jan. 2000).
Amar, Arun P. et al., "Percutaneous Transpedicular Polymethylmethacrylate Vertebroplasty for the Treatment of Spinal Compression Fractures," Neurosurgery 49(5):1105-15 (2001).
Andersen, M. et al., "Vertebroplastik, ny behandling of osteoporotiske columnafrakturer?", Ugeskr laefer 166/6:463-66 (Feb. 2, 2004).
Avalione & Baumeister III, Marks' Standard Handbook for Mechanical Engineers, 10 ed, pp. 5-6 (1996).
Baroud, G. et al., "Injection Biomechanics of Bone Cements Used in Vertebroplasty," Biomaterials & Eng. 00:1-18 (2004).
Baroud, G., "Influence of Mixing Method on the Cement Temperature-Mixing Time History and Doughing Time of Three Acrylic Cements for Vertebroplasty," Wiley Periodicals Inc. 112-116 (2003).
Barr, J.D., "Percutaneous Vertebroplasty for pain Relief and Spinal Stabilization," Spine 25(8):923-28 (2000).
Belkoff, S. et al., The Biomechanics of Vertebroplasty, the Effect of Cement Volume on Mechanical Behavior, SPINE 26(14):1537-41 (2001).
Belkoff, S.M. et al., "An Ex Vivo Biomechanical Evaluation of a Hydroxyapatite Cement for Use with Kyphoplasty," Am. J. Neurorad. 22:1212-16 (2001).
Belkoff, S.M. et al., "An Ex Vivo Biomechanical Evaluation of a Inflatable Bone Tamp Used in the Treatment of Compression Fracture," SPINE 26(2):151-56 (2001).
Belkoff, S.M. et al., "An In Vitro Biomechanical Evaluation of Bone Cements Used in Percutaneous Vertebroplasty," Bone 25(2):235-265 (1999).

(56) References Cited

OTHER PUBLICATIONS

Blinc, A et al., "Methyl-methacrylate bone cement surface does not promote platelet aggregation or plasma coagulation in vitro," Thrombosis Research 114:179-84 (2004).
Bohner, M. et al., "Theoretical and Experimental Model to Describe the Injection of a Polymethacrylate Cement into a Porous Structure," Biomaterials 24(16):2721-30 (2003).
Breusch, S. et al., "Knochenzemente auf Basis von Polymethylmethacrylat," Orthopade 32:41-50 (2003) w/ abs.
Canale et al., "Campbell's operative orthopaedic-vol. 3-ninth ed", Mosby:P2097,2121,2184-85,2890-96, (1998) abstracts.
Carrodegus et al., "Injectable Acrylic Bone Cements for Vertebroplasty with Improved Properties," J. Biomed. Materials Res. 68(1):94-104 (Jan. 2004).
Codman & Shurtleff, "V-MAX.TM. Mixing and Delivery Device," Catalog No. 43-1056.
Cole et al., "AIM Titanium Humeral Nail System," Surgical Technique. DePuy Orthopaedics 17P (2000).
Combs, S. et al., "The Effects of Barium Sulfate on the Polymerization Temperature and Shear Strength of Surgical Simplex P," Clin. Ortho. and Related Res. pp. 287-291 (Jun. 4, 1979).
Cotton, A. et al., "Percutaneous Vertebroplasty: State of the Art," Scientific Exhibit, Radiographics 18:311-20 (1998).
Dean, J.R. et al., "The Strengthening Effect of Percutaneous Vertebroplasty," Clin Radiol. 55:471-476 (2000).
Deramond, H. et al, "Percutaneous Vertebroplasty with Polymethylmethacrylate, Technique Indications and Results," Radiologic Clinics of North America 36(3) (May 1988).
Deramond, H. et al., "Temperature Elevation Caused by Bone cement Polymerization During Vertbroplasty," Bone 25(2):17S-21S (1999).
Grados F. et al.,"Long-Term Observations of Vertebral Osteoporotic Fractures Treated by Percutaneous Vertebroplasty," Rheumatology 39:1410-14 (2000).
Greenberg, "Filling Root Canals by an Injection Technique," Dental Digest 61-63 (Feb. 1963).
Greenberg, "Filling Root Canals in Deciduous Teeth by an Injection Technique," Dental Digest 574-575 (Dec. 1961).
Greig, D., "A New Syringe for Injecting Paraffin," The Lancet 611-12 (Aug. 29, 1903).
Hasenwinkel, J. et al., "A Novel High-Viscosity, Two-Solution Acrylic Bone Cement: Effect of Chemical Composition on Properties," J. Biomed. Materials Research 47(1):36-45 (1999).
Hasenwinkel, J. et al., "Effect of Initiation Chemistry on the Fracture Toughness, Fatigue Strength, and Residual Monomer Content of a Novel High-Viscosity, Two-Solution Acrylic Bone Cement," J. Biomed. Materials Res. 59(3):411-21 (2001).
Heini, P. et al., "Augmentation of Mechanical Properties in Osteoporatic Vertebral Bones—a Biomechanical Investigation of Vertebroplasty Efficacy With Different Bone Cements," EUR Spine J. v. 10, pp. 164-171, Springer-Verlag (2001).
Heini, P., "Percutaneous Transpedicular Vertebroplasty with PMMA: Operative Technique and Early Results," EUR Spine J. v. 9, pp. 445-450, Springer-Verlag (2000).
Heini, P., "The Use of a Side-Opening Injection Cannula in Vertebroplasty," Spine 27(1):105-109 (2002).
Heraeus Palacos ,R, 2008, Palacos R, high Viscosity Bone Cement.
Hernandez et al., "Influence of Powder Particle Size Distribution on Complex Viscosity and Other Properties of Acrylic Bone Cement for Vertebroplasty and Kyphoplasty," J. Biomed. Mat. Res. 77B:98-103 (2006).
Hide, I. et al., "Percutaneous Vertebroplasty: History, Technique and current Perspectives," Clin. Radiology 59:461-67 (2004).
Hu, M. et al., "Kyphoplasty for Vertebral Compression Fracture Via a Uni-Pedicular Approach," Pain Phys. 8:363-67 (2005).
Ishikawa et al., "Effects of Neutral Sodium Hydrogen Phosphate on Setting Reaction and Mechanical Strength of Hydroxyapatite Putty," J. Biomed. Mat. Res. 44:322-29 (199).
Ishikawa et al., "Non-Decay Type Fast-Setting Calcium Phosphate Cement: Hydroxyapatite Putty Containing an Increased Amount of Sodium Alginate," J. Biomed. Mat. Res. 36:393-99 (1997).
Jasper, L.E. et al., "The Effect of Monomer-to-Powder Ratio on the Material Properties of Cranioplastic," Bone 25(2):275-295 (1999).
Jensen, Mary E. et al., "Percutaneous Polymethylmethacrylate Vertebroplasty in the Treatment of Osteoporotic Vertebral Body Compression Fractures: Technical Aspects," AJNJ 18:1897-1904 (1997).
Jensen, Mary E. et al., "Percutaneous Vertebroplasty in the Treatment of Osteoporotic Compression Fractures," Spine Interventions 10(3):547-568 (2000).
Johnson & Johnson Orthopaedics, The CEMVAC Method, Raynham, MA.
Kallmes, D. et al., "Radiation Dose to the Operator During Vertebroplasty: Prospective Comparison of the Use of 1-cc Syringes Versus an Injection Device," AJNR Am. J. Neuroradiol. 24:1257-60 (2003).
Kaufmann et al, "Age of Fracture and Clinical Outcomes of Percutaneous Vertebroplasty," Am. J. Neuroradiology 22:1860-63 (2001).
Krause et al., "The Viscosity of Acrylic Bone Cements," J. Biomed. Mat. Res. 16:219-43 (1982).
Kuhn, Klaus-Dieter, Bone cements—Uptodate Comparison of Physical and Chemical Properties of Commercial Materials, Springer-Verlag Heidelberg Germany (2000).
Kyphom Medical Professionals, KyphXProducts (Nov. 8, 2001).
Lake, R., "The Restoration of the Inferior Turbinate Body by Paraffin Injections in the Treatment of Atrophic Rhinitis," The Lancet 168-69 (Jan. 17, 1903).
Lewis, "Properties of Acrylic Bone Cement: State of the Art Review," J. Biomed. Mat. Res. Appl. Biomaterials 38(2):155-82 (p. 158 s.Viscosity) (1997).
Lewis, "Toward Standardization of Methods of Determination of Fracture Properties of Acrylic Bone Cement and Statistical Analysis of Test Results," J. Biomed. Research: Appl. Biomaterials 53(6):748-68 (2000).
Lewis, G. et al., "Rheological Properties of Acrylic Bone Cement During Curing and the Role of the Size of the Powder Particles," J. Biomed. Mat. Res. Appl. Biomat. 63(2):191-99 (2002).
Li, C. et al., "Thermal Characterization of PMMA-Based Bone Cement Curing," J. Materials Sci.: Materials in Medicine 15:84-89 (2004).
Liang, B. et al., "Preliminary Clinical Application of Percutaneous Vertebroplasty," Zhong Nan Da Xue Bao Yi Xue Ban 31(1):114-9 (2006)(abs. only).
Lieberman, I.H. et al., "Initial Outcome and Efficacy of Kyphoplasty in the Treatment of Painful Osteoporatic Vertebral Compression Fractures," Spine 26(14:1631-38 (2001).
Marks, Standard handbook for mechanical engineers, section 5 (Tenth ed. 1996).
Mathis, John et al., "Percutaneous Vertebroplasty: A Developing Standard of Care for Vertebral Compression Fractures," AJNR Am. J. Neurorad. 22:373-81 (2001).
Medsafe Palacos R 2007, Data Sheet : Palacos R Bone cement with Garamycin pp. 1-7; http://www.medsafe.govt.nz/profs/datasheet/p/palacosbonecements.—htm.
Mousa, W.F. et al., "Biological and Mechanical Properties of PMMA-Based Bioactive Bone Cements," Biomaterials 21:2137-46 (2000).
Noetzel, J. et al., Calcium Phosphate Cements in Medicine and Denistry—A Review of Literature, Schweiz Monatsschr Zehmed 115(12):1148-56 (2005)(abs. only).
Nussbaum et al., "The Chemistry of Acrylic Bone Cements and Implications for Clinical Use in Image-Guided Therapy," J. Vasc. Interv. Radiol. 15:121-26 (2004).
O'Brien, J. et al., "Vertebroplasty in patients with Severe Vertebral Compression Fractures: A Technical Report," AJNR 21:1555-58 (2000).
Varela et al., "Closed Intramedullary Pinning of Metacarpal and Phalanx Fractures," Orthopaedics 13(2):213-15 (1990).

(56) References Cited

OTHER PUBLICATIONS

Vasconcelos, C., "Transient Arterial Hypotension Induced by Polymethyacrylated Injection During Percutaneous Vertebroplasty," Letter to the Editor, JVIR (Aug. 2001).

Walton, A, "Some Cases of Bone Cavities Treated by Stopping With Paraffin," The Lancet 155 (Jan. 18, 1908).

Weissman et al., "Trochanteric Fractures of the Femur Treatment with a Strong Nail and Early Weight-Bearing," Clin. Ortho. & Related Res. 67:143-50 (1969).

Wimhurst, J.A. et al., "Inflammatory Responses of Human Primary Macrophages to Particulate Bone Cements in Vitro," J. Bone & Joint Surgery 83B:278-82 (2001).

Wimhurst, J.A., et al., "The Effects of Particulate Bone Cements at the Bone-Implant Interface," J. Bone & Joint Surgery pp. 588-92 (2001).

Zapalowicz, K. et al., "Percutaneous Vertebroplasty with Bone Cement in the Treatment of Osteoporotic Vertebral Compression Fractures," Ortopedia Traumatologia Rehabilitacja NR Jan. 2003.

Mendizabal et al., Modeling of the curing kinetics of an acrylic bone cement modified with hydroxyapatite. International Journal of Polymeric Materials. 2003;52:927-938.

Morejon et al., Kinetic effect of hydroxyapatite types on the polymerization of acrylic bone cements. International Journal of Polymeric Materials. 2003;52(7):637-654.

Sreeja et al., Studies on poly(methyl methacrylate)/polystyrene copolymers for potential bone cement applications. Metals Materials and Processes. 1996;8(4):315-322.

Yang et al., Polymerization of acrylic bone cement investigated by differential scanning calorimetry: Effects of heating rate and TCP content. Polymer Engineering and Science. Jul. 1997;1182-1187.

Cromer, A, "Fluids", Physics for the Life Sciences, 2:136-37 (1997).

Lindeburg, M., "External Pressurized Liquids", Mechanical Eng Ref Manual for the PE Exam, 10: May 1997.

[No Author Listed] Simplex P Bone Cement. Stryker Corporation, 2 pages, publication date unknown. Retrieved from <http://www.stryker.com/en-us/products/Orthopaedics/BoneCementSubstitutes/index.htm>.

[No Author Listed] Standard Specification for Acrylic Bone Cement. Designation F 451-08, ASTM International (2008), 11 pages.

Juneja, BL, Plastic Deformation of Metals and Related Properties. Chapter 1. New Age International. p. 1-29, 2010.

Kuehn et al., Acrylic bone cements: composition and properties. Orthop Clin North Am. Jan. 2005;36(1):17-28, v.

Lu Orthopedic Bone Cement. Biomechanics and Biomaterials in Orthopedics. Ed. Poitout London: Springer-Verlag London Limited Jul. 2004 86-88.

Su, W.-F, Polymer Size and Polymer Solutions. Principles of Polymer Design and Synthesis. Chapter 2, pp. 9-26, Springer-Verlag Berlin Heidelberg, 2013.

European Search Report for Application No. 12181745.6, dated Sep. 25, 2012. (Docket No. 101896-1270) (9 pages).—( For JP55009242, DE136018, DE868497)).

Japanese Office Action for Application No. 2009-517607, dated Aug. 9, 2011. (4 pages)—(for JP62-68893).

Japanese Office Action for Application No. 2009-517607, dated Aug. 28, 2012. (4 pages)—(for JP0534760Y).

\* cited by examiner

DEVICE FOR DELIVERING VISCOUS MATERIAL

CONTINUING DATA

This application claims the benefit of co-pending U.S. Ser. No. 10/947,496, entitled "Device for Delivering Viscous Material", filed Sep. 22, 2004, which claims the benefit of U.S. Provisional Application No. 60/507,290 filed on Sep. 26, 2003, each of which is hereby incorporated by reference in its entirety.

FIELD OF THE INVENTION

This application relates to medical tools and methods, in particular to medical instruments and methods for delivering a viscous material to a site within a patient.

BACKGROUND OF THE INVENTION

One example of delivering a viscous material to a medical site is in a vertebroplasty procedure. Typically, the clinician seeks to treat a compression fracture of a vertebral body by injecting bone cement, a highly viscous material into a fracture site. In order to assure that the injected cement does not travel far from its intended placement location, fluoroscopy is often used by the clinician to monitor the location of the injected cement. However, delivering the cement by simple syringe would require the clinician to place his hand in the fluoroscopy field causing the clinician to be exposed to significant radiation produced by the fluoroscope during delivery of the cement to the surgical site. Thus, in order to reduce such exposure, the clinician often performs this procedure when the fluoro is turned off, and only monitors the cement location intermittently when safely outside the range of the fluoroscopy field.

Known techniques for keeping the clinician outside the fluoro field typically involve the use of a long extension tube, whereby one end of the tube extends from an injection pump and the other end is coupled to a hollow bone needle. The extension tube is used as a conduit for delivering the bone cement from the pump to the bone needle for injection into the vertebral body. The additional length of the extension tube allows a clinician to perform the vertebroplasty at a distance outside the fluoro field.

A disadvantage of such injection devices is that the cement is a highly viscous material requiring a high force to move the cement through the tube, resulting in a high-pressure build up within the device. The pressure build-up increases the effort need to inject the cement and decreases the natural feedback to the clinician. For example, the lack of natural feedback can cause the clinician to inadvertently leak bone cement into the surrounding tissue or the spinal cord itself, resulting in a number of serious health risks. Furthermore, the additional length of tube makes such injection devices susceptible to premature curing or hardening, resulting in the tube becoming clogged.

SUMMARY OF THE INVENTION

In accordance with the present invention, there is provided a device for delivering a viscous material into a site in a patient, comprising:
an actuator including an actuator vessel;
a delivery tube, having a first end, a second end and an inner bore, wherein the first end is coupled to the actuator; and
a container having a connection port for connecting to the second end of the tube and an exit port.

In accordance with the present invention, there is provided a device for delivering a viscous material comprising:
a delivery tube having a first end portion, a second end portion, and an inner bore therebetween, the first end portion adapted to contain an incompressible fluid and the second end portion adapted to contain a viscous material.

In accordance with the present invention, there is provided a method of delivering a viscous material under fluoroscopy to a site in a patient comprising the steps of:
a) providing a delivery tube containing an incompressible fluid and a viscous material, wherein the viscous material is located within the fluoroscopy field; and
b) pressurizing the incompressible fluid outside the fluoroscopy field to exert pressure on the viscous material.

In accordance with the present invention, there is provided a method of delivering a viscous material to a site in a patient comprising the steps of:
a) providing a device having an actuator, a delivery tube filled with an incompressible fluid and a container;
b) filling the container with a viscous material; and
c) activating the actuator to pressurize the fluid to exert a force on the viscous material.

In accordance with the present invention, there is provided a device for delivering a viscous material into a site in a patient, comprising:
a) a delivery tube, having a first end, a second end and an inner bore,
b) an incompressible fluid contained within the inner bore of the delivery tube,
c) a container having a connection port for connecting to the second end of the delivery tube, an inner bore, an exit port,
d) a viscous material contained within the inner bore of the container, and
e) a separator sized to move within the inner bore of the container for separating a viscous material from the incompressible fluid.

In accordance with the present invention, there is provided a device for delivering a viscous material into a site in a patient, comprising:
a) a delivery tube, having a first end, a second end and an inner bore,
b) a first fluid contained within the inner bore of the delivery tube, and
c) a container having a connection port for connecting to the second end of the delivery tube, an inner bore, an exit port, and
d) a second fluid contained within the inner bore of the container.

In accordance with the present invention, there is provided a device for delivering a viscous material into a site in a patient, comprising:
a) a container having a connection port for connecting to the second end of the delivery tube, an inner bore, an exit port adapted for connection to the patient,
b) a separator housed within the inner bore, thereby defining a distal bore and an proximal bore,
c) a first fluid contained within the proximal bore of the container.

Disclosed herein are tools and methods for delivering a viscous material to a site within a patient. The methods and devices of the present invention are particularly advantageous in that they can safely remove the clinician from the fluoro field while providing the clinician with visual and mechanical feedback while injecting the material into the patient. Such features minimize safety concerns to the patient and the clinician.

In one embodiment, the invention is a device for delivering a viscous material into a site in a patient, including an actuator with an actuator vessel; a delivery tube, having a first end, a second end and an inner bore, wherein the first end is coupled to the actuator; and a container having a connection port for connecting to the second end of the tube and an exit port.

In another exemplary embodiment, the present invention is a device for delivering a viscous material comprising a delivery tube having a first end portion, a second end portion, and an inner bore therebetween, the first end portion adapted to contain an incompressible fluid and the second end portion adapted to contain a viscous material.

Another embodiment of the present invention is a device for delivering a viscous material into a site in a patient, having a delivery tube, with a first end, a second end and an inner bore, an incompressible fluid contained within the inner bore of the delivery tube, a container with a connection port for connecting to the second end of the delivery tube, an inner bore, an exit port, a viscous material contained within the inner bore of the container, and a separator sized to move within the inner bore of the container for separating a viscous material from the incompressible fluid.

Another embodiment of the present invention is a device for delivering a viscous material into a site in a patient, having a delivery tube, with a first end, a second end and an inner bore, a first fluid contained within the inner bore of the delivery tube, and a container with a connection port for connecting to the second end of the delivery tube, an inner bore, an exit port, and a second fluid contained within the inner bore of the container.

In yet another embodiment of the present invention the device for delivering a viscous material into a site in a patient, has a container having a connection port for connecting to the second end of the delivery tube, an inner bore, an exit port adapted for connection to the patient, a separator housed within the inner bore, thereby defining a distal bore and an proximal bore, a first fluid contained within the proximal bore of the container.

In other aspects of the present invention, a method of delivering a viscous material under fluoroscopy to a site in a patient comprises the steps of providing a delivery tube containing an incompressible fluid and a viscous material, wherein the viscous material is located within the fluoroscopy field; and pressurizing the incompressible fluid outside the fluoroscopy field to exert pressure on the viscous material.

BRIEF DESCRIPTION OF THE DRAWINGS

These and other features and advantages of the methods and instruments disclosed herein will be more fully understood by reference to the following detailed description in conjunction with the attached drawings in which like reference numerals refer to like elements through the different views. The drawings illustrate principles of the methods and instruments disclosed herein and, although not to scale, show relative dimensions.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention is directed to devices and methods for remotely delivering a viscous material to a targeted site in a patient. In general, the device is a delivery tube containing two materials, the viscous material to be injected into the patient and an incompressible fluid to act on the viscous material. The end of the tube containing the viscous material is placed at the delivery site while the other end of the delivery tube extends outside the fluoro field. The clinician can then safely activate the movement of the material into the patient from outside the fluoro field. The amount of pressure needed to deliver the material is also reduced because the material does not have to travel the entire distance through the tube from outside the fluoro field, resulting in a decrease in friction between the tube and the viscous material. Additionally, the present invention enables the viscosity of the viscous material to be higher because of the noncompliance of the tube and the positioning of the material with respect to the targeted delivery site.

Figure 1:
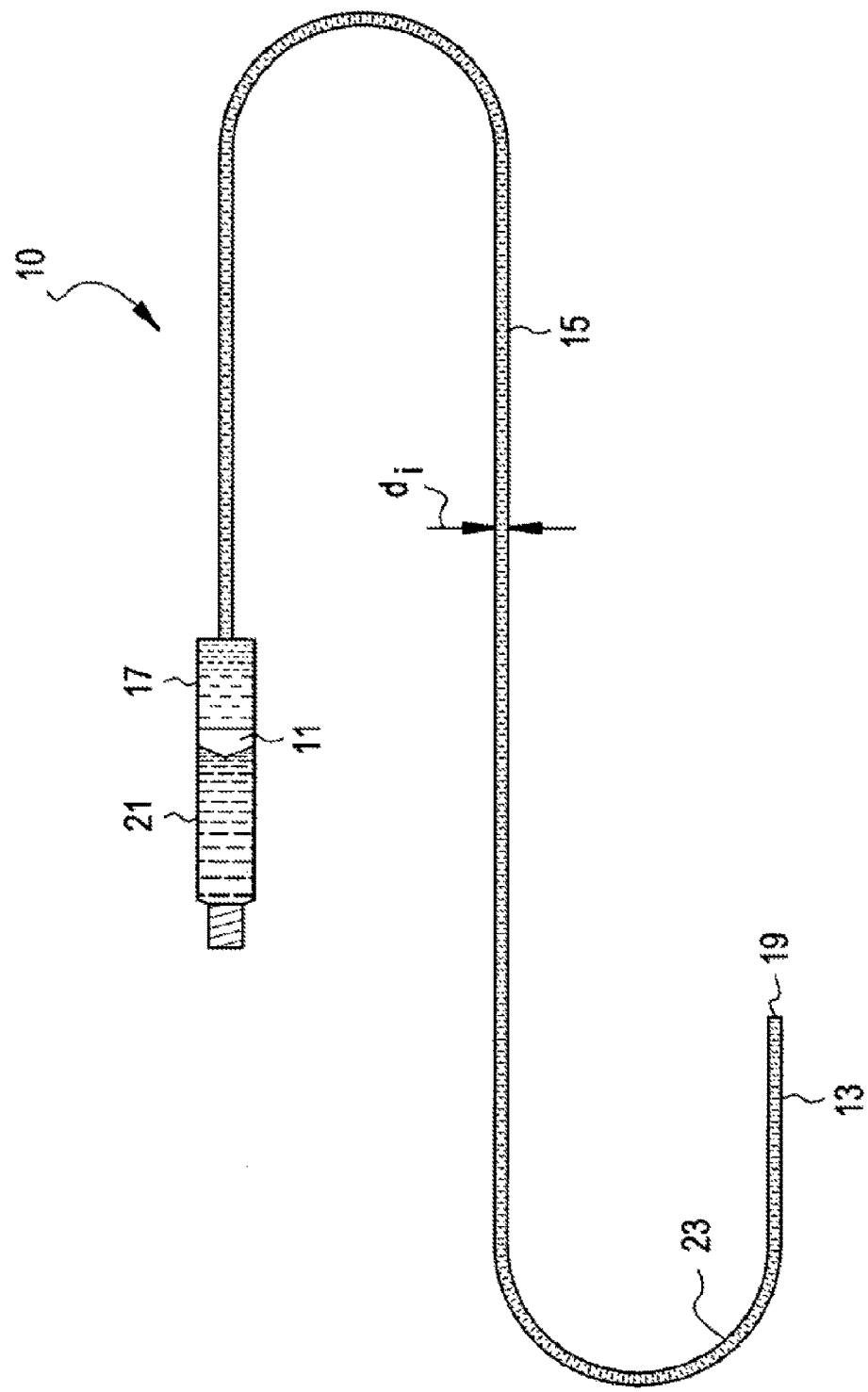
FIG. 1 is a schematic of a device for delivering a viscous material according to one embodiment of the present invention.

FIG. 1 illustrates an exemplary embodiment of a delivery device. As shown the delivery device 10 includes a delivery tube 15 having a first end portion 13 and a second end portion 17 and an inner bore 19 defined therebetween. The tube 15 is adapted to contain an incompressible fluid 23 at the first end portion 13 and a viscous material 21 at the second end portion 17. The delivery device may be connected to a cannula seated at the delivery site in the patient.

The delivery tube can further include a separator 11 within the bore of the tube for separating the viscous material from the incompressible fluid. The separator 11 is slidably movable within the bore 19 of the tube.

The delivery tube 15 is preferably flexible so as to allow the tube to be of a length sufficiently long enough to place the clinician outside the fluoroscopy field and to minimize the amount of torque at the second end portion produced by any off-axis movement in relation to the cannula. Additionally, the tube is noncompliant to minimize the amount of viscous material that is delivered after actuation of the material is stopped. A preferred material for the construction of the delivery tube is PEEK, however, nylon, polypropylenes, and polytetraflouroethylenes (PTFE) or other fluorinated polycarbons could also be used. Any materials, which are durable, sterilizable, biofriendly, chemically compatible with viscous materials such as bone cement and substantially noncompliant under the expected operating pressures of up to 1200 psi, but could, also withstand pressures up to 5000 psi.

The tubing may be reinforced with a non-stretch coil or a braid such that together as a unit, the tube and reinforcing coil or braid exhibit less than a 10% change in volume under operating pressures of about 1200 psi, compared to their initial volume under atmospheric pressure. The reinforcing coil or braid can be formed from stainless steel, nitinol, titanium, nylon or polymers such as aramid fibers, KEVLAR fibers, etc.) or other biocompatible materials having the same nonstretch characteristics described above.

In some embodiments, the inner bore 19 of the delivery tube 15 has a diameter $d_i$ that is in the range of 1 to 10 mm, and preferably in the range of 2.5 to 5 mm. The smaller the diameter, the more flexible the tube will be when delivering the viscous material. The length of the delivery tube $l_T$ is at least 20 cm and more preferably between 20 and 60 cm. In this range the clinician may be placed safely outside the fluoroscopy field.

The delivery tube contains an incompressible fluid 23 or hydraulic fluid such as water, water and oil emulsion, water-glycol mixture, straight synthetic fluid (e.g., silicone or phosphate esters, ester blends, and chlorinated hydrocarbon-based fluids) or petroleum oil. Preferably, the incompressible fluid contained within the delivery tube is saline. The incompressible property of the fluid allows for a force generated at the first or proximal end of the delivery tube to be transferred to the viscous material. The incompressible fluid can be pre-filled and sealed within the delivery tube prior to use by the clinician or the clinician can fill the tube at the time of use.

In some embodiments, the device of the present invention is used to deliver a viscous material such as bone cement into a fractured vertebral body. The bone cement may be any material typically used to augment vertebral bodies, including acrylic based bone cements (such as PMMA-based bone cements), pastes comprising bone particles (either mineralized or demineralized or both); and ceramic based bone cements (such as hydroxyapatite and TCP based pastes). The present invention enables an increase in the acceptable viscosity of the cement to be delivered because of the substantial noncompliance within the delivery tube and the location of the cement close to the actual delivery site. The viscous material is contained within the device such that it is in the fluoroscopy field at all times during the procedure.

In some embodiments, as shown in FIG. 1 the delivery tube preferably includes a separator 11 located within the inner bore of the delivery tube between the incompressible fluid and the viscous material. The separator is movable and slidable within the inner bore. A force generated on the incompressible fluid will transfer through the fluid to the separator and then to the viscous material to deliver the material to the desired location. A person skilled in the art will understand that the separator is not needed to transfer the force to the viscous material. In one embodiment the separator is a piston.

Figure 2:
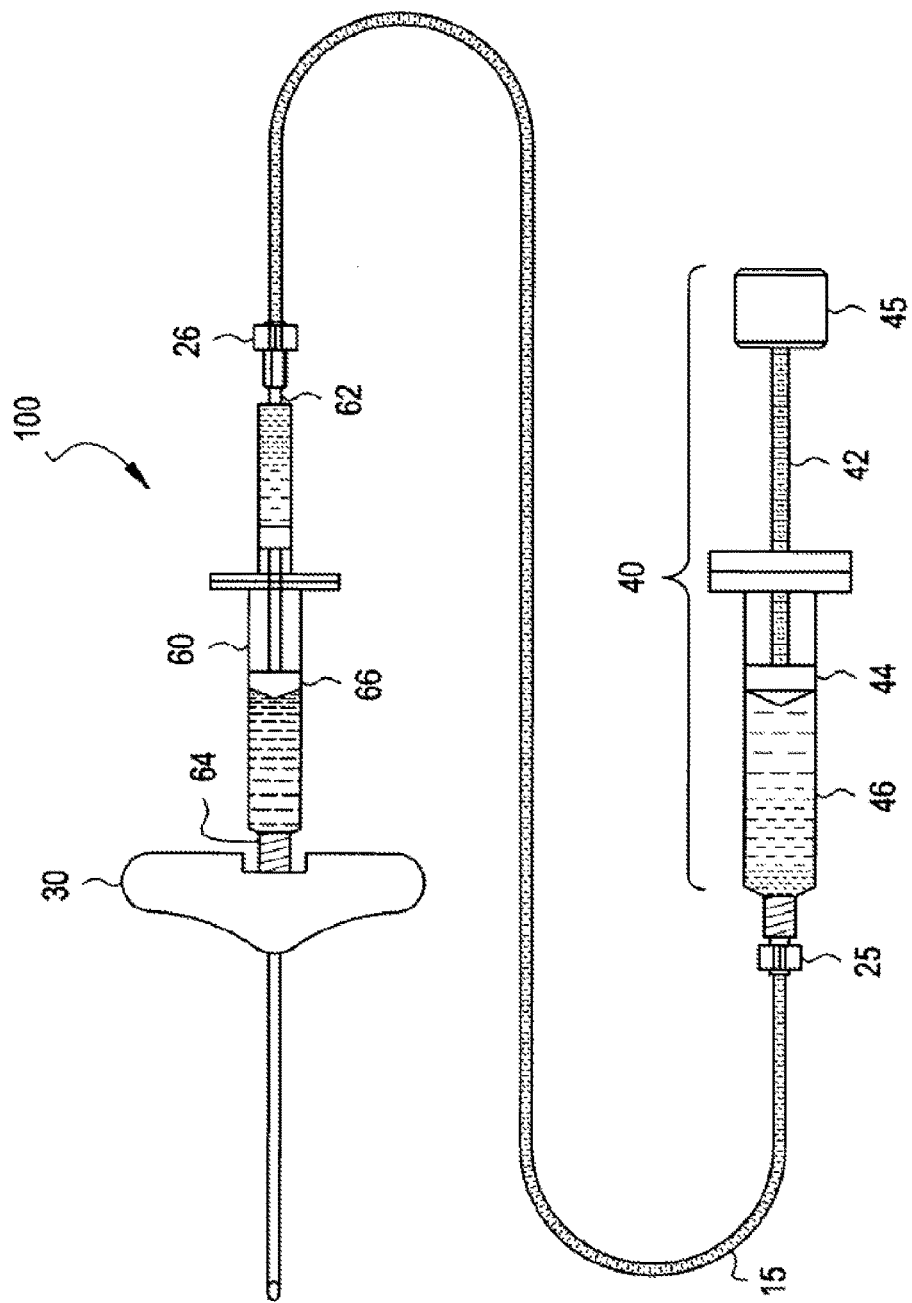
FIG. 2 is a schematic of another embodiment of a device for delivering a viscous material connected to a cannula.

In an alternate embodiment of the present invention shown in FIG. 2, the delivery device 100 comprises an actuator 40 including an actuator vessel, a delivery tube 15, and a container 60. The tube is preferably filled with an incompressible fluid 23. The first end portion of the tube has a sealing connector 25 to connect to the actuator 40 and the second end portion of the tube has another sealing connector 26 to connect to the container 60. The container can be connected to a cannula 30 for positioning at the delivery site within the patient. The container is adapted to hold the viscous material to be delivered. The device can be packaged sterile and can be disposable.

In the illustrated embodiment shown in FIG. 2, the actuator 40 is linear and includes a knob 45, a threaded rod 42 mounted to an actuator vessel 46 containing the fluid to be pressurized. The distal end of the threaded rod 42 is attached to a plunger 44. The plunger 44 is slidably received within the vessel 46. The vessel is sized to hold a volume of fluid at least as much as the amount of viscous material to be delivered. Preferably, the vessel is sized to hold between 2 and 25 cc of fluid. As the threaded rod is advanced through the vessel, the plunger comes into contact and exerts force on the fluid pushing the fluid out of the vessel, through the delivery tube and into contact with the viscous material in the container. Preferably, the vessel is made from a material that is noncompliant such as PEEK or a polycarbonate.

In some embodiments, the actuator vessel 46 includes a visualization window (not shown) so that the user can observe the movement of the fluid as the actuator is engaged and the viscous material is delivered to the patient. Using a noncompliant system and an incompressible fluid results in the flow of the fluid to be the same as the flow of the viscous material so that 1 cc of fluid moved from the vessel correlates with 1 cc of viscous material moving out of the container. Other embodiments for viewing the amount of material delivered can include graduation lines on the outside of the vessel indicating the volume of material exiting the container. When the plunger tip reaches one of the graduation lines the clinician can determine the amount of material delivered. For actuators that use rotation to advance the plunger, a rotational scale could be used such that one turn of the actuator would correlate to a set amount of material exiting the container. A digital or analog counter could also be used to translate the movement of the plunger into the actual amount of viscous material delivered.

A person skilled in the art will appreciate that other actuators can be used in the device. Examples of linear actuators include a rack and pinion, ratchet and pawl, an electric motor with a worm gear, an angled clutch plate on a rod, or a walking beam. An example of a nonlinear actuator that could also be used is a hydraulic pump.

The delivery tube 15 has the same tube characteristics and design features as described in the embodiment shown in FIG. 1.

In some embodiments the delivery tube 15 has a sealing connector 26 at the second end for connecting to a container 60. Preferably this connector is a Luer-lock type of fitting. Likewise in some embodiments, the delivery tube 15 has another sealing connector 25 at the first end for connecting to an actuator vessel 46. Preferably this connector is also a Luer-lock type of fitting.

The container 60 holds the viscous material to be delivered to the patient. The container may be filled with the viscous material by any number of conventional filling procedures. The container has a connection port 62 for coupling with the delivery tube 15 and an exit port 64 for the viscous material to exit through and for coupling with the cannula 30. Preferably, the container holds between 2 and 20 cc of viscous material. The container is also made from any noncompliant material but the material also has to be biocompatible with the viscous material. Accordingly the container can be made from the following materials: nylon, polyphenylene sulfide (PPS), ultrahigh molecular weight polyethylene, cyclic Olefin copolymer (COC) liquid crystalline polymer (LCP) acetal copolymers (POM), and polybutylene terephthalate (PBT). In some embodiments multiple containers can be filled with the viscous material and interchanged by the clinician as one is emptied. A separator 66 may be located in the container to separate the viscous material from the fluid so that the force is transferred through the separator to the viscous material pushing it out of the exit port to the desired delivery site within the patient. In one exemplary embodiment the separator is a piston.

In one embodiment, the container 60 is translucent allowing the clinician to visualize the viscous material at all times during delivery of the material. In an alternate embodiment, the container is color tinted and the separator inside the container is colored so that as the separator travels through the container pushing the viscous material out, there is a resultant color displayed that the clinician can visualize from outside the fluoro field. Alternately, a linear transducer could be used to display the path the separator travels as it advances through the container.

Figure 3:
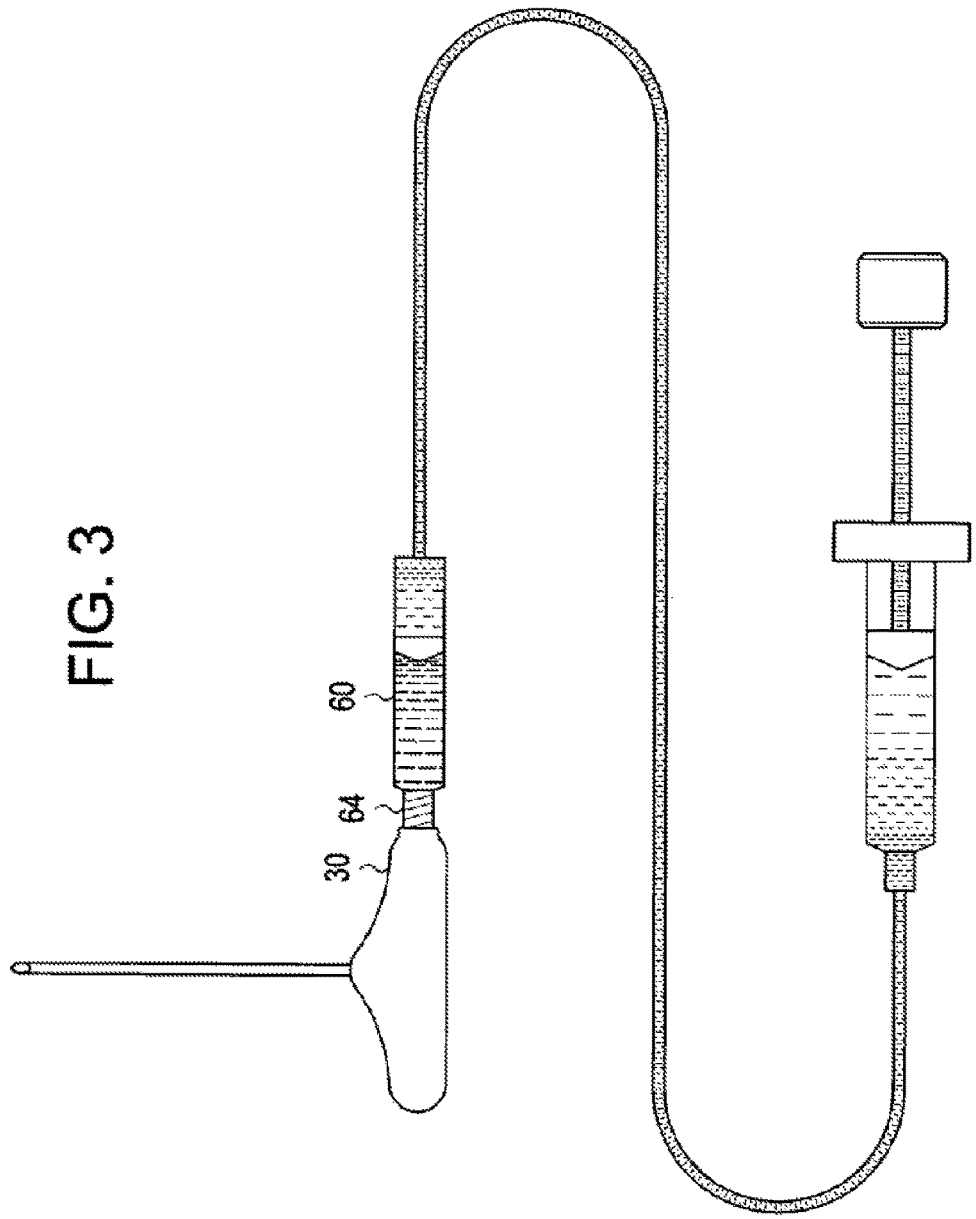
FIG. 3 is a schematic of the device shown in FIG. 2 connected to a cannula at an angle.

The container can connect to a cannula through the exit port 64. The connection between the container and the cannula is preferably made at an angle between 80 and 135 degrees, to move the container and delivery tube out of the way of the clinician and minimize interference with the imaging device. As shown in FIG. 3 the container connects to the cannula at approximately a 90-degree angle.

In another embodiment of the present invention, the delivery tube is connected to a stopcock to allow two containers at two implant sites within the same patient to be connected to the device allowing delivery of the viscous material to two sites without having to stop the procedure to disconnect and connect another container of material.

Figure 4:
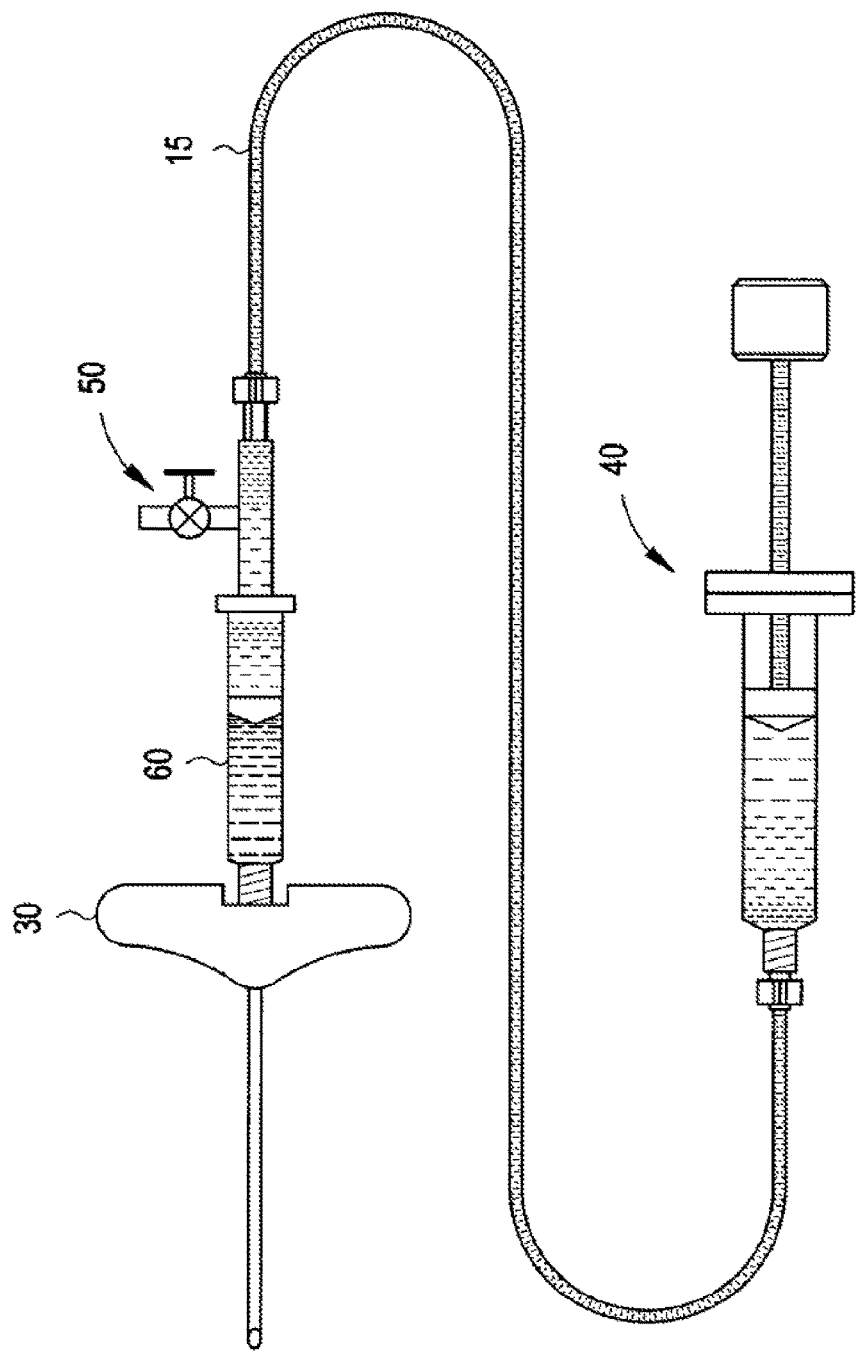
FIG. 4 is a schematic of another embodiment of the present invention including a pressure relief valve.

Excess pressure build up in the system has the potential to cause the device to fail resulting in possible harm to the patient or the clinician. Accordingly, in some embodiments of the invention, a safety mechanism for preventing excess pressure buildup can also be added to the device. One example of a safety mechanism is an in line pressure relief valve with a cracking pressure such that when an unsafe operating pressure is reached the valve will open and divert the pressurized fluid into a catch reservoir. The valve could use a spring force or membrane that ruptures to establish the cracking pressure. Another option shown in FIG. 4 would be to include a pressure relief valve 50 that the user can use at his discretion to divert pressure for example at the end of the procedure to ensure that extra viscous material is not inadvertently delivered. It is to be understood that the pressure relief valve could be placed anywhere along the fluid path.

There may also be a pressure monitoring means connected to the device so that the user can see when the pressure is becoming excessive. An example of a pressure monitoring means can be a gauge in the delivery tube that displays the instantaneous pressure or a binary indicator that visually indicates when the pressure is ok and when it has exceeded the limit.

Another example of a safety mechanism would be a torque-limiting device that would prevent the user from generating excessive force on the fluid. A clutch type mechanism could be used with a screw type actuator to slip when a certain torque was reached. A break away handle could be used if the device was driven similar to a caulking gun.

In one embodiment the device is pre-assembled such that the incompressible fluid is pre-filled and sealed within the delivery tube and the actuator vessel. In another embodiment, the delivery tube and actuator vessel are empty and the user would fill with the incompressible fluid. In all embodiments the viscous material would be placed in the container at the time of use.

An exemplary embodiment of a method for delivering a viscous material to a site within a patient is providing a device having an actuator, a delivery tube filled with an incompressible fluid, and a container; filling the container with a viscous material, and activating the actuator of the device to pressurize the fluid in the delivery tube to push the viscous material out of the container.

Another embodiment of a method for delivering a viscous material under fluoroscopy to a site in a patient includes the steps of providing a delivery tube containing an incompressible fluid and a viscous material, wherein the viscous material is located within the fluoroscopy field; and pressurizing the incompressible fluid outside the fluoroscopy field to exert pressure on the viscous material.

As previously stated, a person skilled in the art will appreciate that the method can be performed in any sequence using any of the steps. Moreover, the devices of the present invention can be used to perform a variety of other surgical procedures not illustrated or described herein.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for delivering a viscous material into a site in a patient, comprising:
   an actuator including an actuator vessel and an electric motor;
   a delivery tube, having a first end, a second end and an inner bore, wherein the first end is coupled to the actuator;
   a plunger housed within the delivery tube, and
   a container having a connection port for connecting to the second end of the delivery tube and an exit port, and containing a viscous material, wherein the viscous material is a PMMA-based bone cement, and
   wherein the actuator is adapted to advance the plunger.

2. The system of claim 1, wherein the actuator comprises a linear actuator.

3. The system of claim 1, wherein the actuator comprises a hydraulic pump.

4. The system of claim 1, wherein the actuator has a visualization window for viewing the contents of the vessel.

5. The system of claim 4, wherein the visualization window has means for measuring the amount of viscous material being delivered.

6. The system of claim 5, wherein the means for measuring are graduation lines marked on the outside of the actuator.

7. The system of claim 1, wherein the delivery tube is made of PEEK.

8. The system of claim 1, wherein the delivery tube has an inner diameter between 1 and 10 mm.

9. The system of claim 1, wherein the container is adapted to hold between 2 and 20 cc of viscous material.

10. The system of claim 1, wherein the container further comprises a visualization window for viewing contents of the container.

11. The system of claim 10, wherein the visualization window has means for measuring the amount of viscous material being delivered.

12. The system of claim 11, wherein the means for measuring are graduation lines marked on the outside of the container.

13. The system of claim 1, wherein the container is made from a noncompliant material.

14. The system of claim 1, further comprising a pressure monitor.

15. The system of claim 14, wherein the pressure monitor is a gauge connected to the delivery tube.

16. The system of claim 1, further comprising a pressure relief valve.

17. The system of claim 16, wherein the pressure relief valve opens when an unsafe pressure is reached and diverts the viscous material to a catch reservoir.

18. The system of claim 1, further comprising a cannula for delivery of the viscous material to the site in the patient.

19. The system of claim 18, wherein the cannula connects to the exit port of the container at an angle between 80 and 135 degrees.

20. The system of claim 18, further comprising a second cannula for delivery of the viscous material to a second site in the patient.

\* \* \* \* \*